United States Patent
Sarantos et al.

(10) Patent No.: US 9,392,946 B1
(45) Date of Patent: Jul. 19, 2016

(54) HEART RATE SENSOR WITH HIGH-ASPECT-RATIO PHOTODETECTOR ELEMENT

(71) Applicant: Fitbit, Inc., San Francisco, CA (US)

(72) Inventors: Chris H. Sarantos, San Francisco, CA (US); Peter W. Richards, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/724,750

(22) Filed: May 28, 2015

(51) Int. Cl.
*A61B 5/024* (2006.01)
*A61B 5/00* (2006.01)

(52) U.S. Cl.
CPC ......... *A61B 5/02427* (2013.01); *A61B 5/02438* (2013.01); *A61B 5/681* (2013.01)

(58) Field of Classification Search
CPC . A61B 5/02427; A61B 5/02438; A61B 5/681
See application file for complete search history.

(56) References Cited

U.S. PATENT DOCUMENTS

| | | | |
|---|---|---|---|
| 4,367,752 A | 1/1983 | Jimenez et al. |
| 4,771,792 A | 9/1988 | Seale |
| 5,036,856 A | 8/1991 | Thornton |
| 5,101,831 A | 4/1992 | Koyama et al. |
| 5,318,597 A | 6/1994 | Hauck et al. |
| 5,738,104 A | 4/1998 | Lo et al. |
| 6,076,015 A | 6/2000 | Hartley et al. |
| 6,131,076 A | 10/2000 | Stephan et al. |
| 6,241,684 B1 | 6/2001 | Amano et al. |
| 6,289,230 B1 | 9/2001 | Chaiken et al. |
| 6,402,690 B1 | 6/2002 | Rhee et al. |
| 6,418,394 B1 | 7/2002 | Puolakanaho et al. |
| 6,583,369 B2 | 6/2003 | Montagnino et al. |
| 6,731,967 B1 | 5/2004 | Turcott |
| 6,997,882 B1 | 2/2006 | Parker et al. |
| 7,539,532 B2 | 5/2009 | Tran |
| 7,720,306 B2 | 5/2010 | Gardiner et al. |
| 8,040,758 B1 | 10/2011 | Dickinson |
| 8,152,745 B2 | 4/2012 | Smith et al. |
| 8,172,761 B1 | 5/2012 | Rulkov et al. |
| 8,211,503 B2 | 7/2012 | Tsao et al. |
| 8,346,328 B2 | 1/2013 | Mannheimer et al. |
| 8,386,042 B2 | 2/2013 | Yudovsky et al. |
| 8,444,578 B2 | 5/2013 | Bourget et al. |
| 8,475,367 B1 | 7/2013 | Yuen et al. |

(Continued)

FOREIGN PATENT DOCUMENTS

CN 101615098 A 12/2009
CN 102389313 A 3/2012

(Continued)

OTHER PUBLICATIONS

U.S. Appl. No. 14/214,655, filed Mar. 14, 2014, Hong et al.

(Continued)

*Primary Examiner* — Bo J Peng
(74) *Attorney, Agent, or Firm* — Weaver Austin Villeneuve & Sampson LLP

(57) ABSTRACT

Heart rate sensors including high-aspect-ratio photodetector elements are discussed herein. Such high-aspect-ratio photodetector elements may provide improved signal-strength-to-power-consumption performance for heart rate sensors incorporating such photodetector elements as compared with heart rate sensors incorporating, for example, square photodetector elements.

30 Claims, 14 Drawing Sheets

(56) References Cited

U.S. PATENT DOCUMENTS

| | | | |
|---|---|---|---|
| 8,579,827 B1 | 11/2013 | Rulkov et al. |
| 8,792,981 B2 | 7/2014 | Yudovsky et al. |
| 8,868,377 B2 | 10/2014 | Yuen et al. |
| 8,920,332 B2 | 12/2014 | Hong et al. |
| 8,945,017 B2 | 2/2015 | Venkatraman et al. |
| 8,948,832 B2 | 2/2015 | Hong et al. |
| 8,954,135 B2 | 2/2015 | Yuen et al. |
| 8,956,303 B2 | 2/2015 | Hong et al. |
| 8,998,815 B2 | 4/2015 | Venkatraman et al. |
| 9,005,129 B2 | 4/2015 | Venkatraman et al. |
| 9,042,971 B2 | 5/2015 | Brumback et al. |
| 9,044,149 B2 | 6/2015 | Richards et al. |
| 9,044,150 B2 | 6/2015 | Brumback et al. |
| 9,049,998 B2 | 6/2015 | Brumback et al. |
| 9,089,760 B2 | 7/2015 | Tropper et al. |
| 9,113,794 B2 | 8/2015 | Hong et al. |
| 9,113,795 B2 | 8/2015 | Hong et al. |
| 9,237,855 B2 | 1/2016 | Hong et al. |
| 2001/0044588 A1 | 11/2001 | Mault |
| 2003/0163710 A1 | 8/2003 | Ortiz et al. |
| 2004/0236227 A1 | 11/2004 | Gueissaz |
| 2005/0054940 A1 | 3/2005 | Almen |
| 2005/0245793 A1 | 11/2005 | Hilton et al. |
| 2006/0195020 A1 | 8/2006 | Martin et al. |
| 2007/0213020 A1 | 9/2007 | Novac |
| 2007/0265533 A1 | 11/2007 | Tran |
| 2008/0097221 A1 | 4/2008 | Florian |
| 2009/0012433 A1 | 1/2009 | Fernstrom et al. |
| 2009/0132197 A1 | 5/2009 | Rubin et al. |
| 2009/0163783 A1 | 6/2009 | Mannheimer et al. |
| 2009/0292332 A1 | 11/2009 | Li et al. |
| 2009/0318779 A1 | 12/2009 | Tran |
| 2010/0106044 A1 | 4/2010 | Linderman |
| 2010/0152600 A1 | 6/2010 | Droitcour et al. |
| 2010/0204550 A1 | 8/2010 | Heneghan et al. |
| 2010/0249633 A1 | 9/2010 | Droitcour et al. |
| 2010/0274100 A1 | 10/2010 | Behar et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | McCombie et al. |
| 2010/0298661 A1 | 11/2010 | McCombie et al. |
| 2010/0331145 A1 | 12/2010 | Lakovic et al. |
| 2010/0331657 A1 | 12/2010 | Mensinger et al. |
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2011/0112442 A1 | 5/2011 | Meger et al. |
| 2011/0118621 A1 | 5/2011 | Chu |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |
| 2012/0232432 A1 | 9/2012 | Kahn et al. |
| 2012/0245439 A1 | 9/2012 | Andre et al. |
| 2012/0253486 A1 | 10/2012 | Niemimaki |
| 2012/0255875 A1 | 10/2012 | Vicente et al. |
| 2012/0274508 A1 | 11/2012 | Brown et al. |
| 2012/0316471 A1 | 12/2012 | Rahman et al. |
| 2013/0009779 A1 | 1/2013 | Wittling et al. |
| 2013/0073254 A1 | 3/2013 | Yuen et al. |
| 2013/0073255 A1 | 3/2013 | Yuen et al. |
| 2013/0077826 A1 | 3/2013 | Cowperthwaite et al. |
| 2013/0080113 A1 | 3/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0191034 A1 | 7/2013 | Weast et al. |
| 2013/0211265 A1 | 8/2013 | Bedingham et al. |
| 2013/0218053 A1 | 8/2013 | Kaiser et al. |
| 2014/0073486 A1 | 3/2014 | Ahmed et al. |
| 2014/0074431 A1 | 3/2014 | Modi |
| 2014/0099614 A1 | 4/2014 | Hu et al. |
| 2014/0107493 A1 | 4/2014 | Yuen et al. |
| 2014/0135631 A1 | 5/2014 | Brumback et al. |
| 2014/0142403 A1 | 5/2014 | Brumback et al. |
| 2014/0241626 A1 | 8/2014 | Sull et al. |
| 2014/0275821 A1 | 9/2014 | Beckman |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278139 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0303523 A1 | 10/2014 | Hong et al. |
| 2014/0378786 A1 | 12/2014 | Hong et al. |
| 2014/0378787 A1 | 12/2014 | Brumback et al. |
| 2014/0378872 A1 | 12/2014 | Hong et al. |
| 2015/0025393 A1 | 1/2015 | Hong et al. |
| 2015/0025394 A1 | 1/2015 | Hong et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230761 A1 | 8/2015 | Brumback et al. |
| 2016/0034634 A9 | 2/2016 | Hong et al. |

FOREIGN PATENT DOCUMENTS

| | | | |
|---|---|---|---|
| CN | 103093420 A | 5/2013 |
| EP | 1 721 237 | 8/2012 |

OTHER PUBLICATIONS

U.S. Appl. No. 14/724,750, filed May 28, 2015, Sarantos et al.

US Office Action, dated Aug. 4, 2014, issued in U.S. Appl. No. 13/924,784.

US Notice of Allowance, dated Nov. 19, 2014, issued in U.S. Appl. No. 13/924,784.

US Office Action, dated Oct. 22, 2014, issued in U.S. Appl. No. 14/290,884.

US Notice of Allowance, dated Feb. 6, 2015, issued in U.S. Appl. No. 14/290,884.

US Office Action, dated Jun. 22, 2015, issued in U.S. Appl. No. 14/693,710.

US Notice of Allowance, dated Jul. 27, 2015, issued in U.S. Appl. No. 14/693,710.

US Notice of Allowance, dated Sep. 23, 2014, issued in U.S. Appl. No. 14/292,669.

US Notice of Allowance (Corrected Notice of Allowability), dated Oct. 14, 2014, issued in U.S. Appl. No. 14/292,669.

US Notice of Allowance (Corrected Notice of Allowability), dated Dec. 31, 2014, issued in U.S. Appl. No. 14/292,669.

US Notice of Allowance, dated Oct. 14, 2014, issued in U.S. Appl. No. 14/295,144.

US Notice of Allowance, dated Dec. 3, 2014, issued in U.S. Appl. No. 14/295,144.

US Notice of Allowance, dated Sep. 26, 2014, issued in U.S. Appl. No. 14/295,158.

US Notice of Allowance (Corrected Notice of Allowability), dated Dec. 31, 2014, issued in U.S. Appl. No. 14/295,158.

US Office Action, dated Jan. 23, 2015, issued in U.S. Appl. No. 14/507,184.

US Final Office Action, dated May 11, 2015, issued in U.S. Appl. No. 14/507,184.

US Notice of Allowance, dated Aug. 11, 2015, issued in U.S. Appl. No. 14/507,184.

US Office Action, dated Jan. 26, 2015, issued in U.S. Appl. No. 14/295,161.

(56) References Cited

OTHER PUBLICATIONS

US Notice of Allowance, dated Apr. 14, 2015, issued in U.S. Appl. No. 14/295,161.
US Notice of Allowance, dated Jul. 28, 2015, issued in U.S. Appl. No. 14/295,161.
US Office Action, dated May 11, 2015, issued in U.S. Appl. No. 14/673,630.
US Office Action, dated Jan. 27, 2015, issued in U.S. Appl. No. 14/507,173.
US Notice of Allowance, dated Apr. 17, 2015, issued in U.S. Appl. No. 14/507,173.
US Notice of Allowance (Corrected Notice of Allowability), dated Jul. 16, 2015, issued in U.S. Appl. No. 14/507,173.
US Office Action, dated Jun. 8, 2015, issued in U.S. Appl. No. 14/673,634.
US Office Action, dated Aug. 5, 2014, issued in U.S. Appl. No. 14/292,673.
US Notice of Allowance, dated Dec. 8, 2014, issued in U.S. Appl. No. 14/292,673.
US Notice of Allowance (Corrected Notice of Allowability), dated Mar. 5, 2015, issued in U.S. Appl. No. 14/292,673.
US Office Action, dated Sep. 18, 2014, issued in U.S. Appl. No. 14/295,059.
US Notice of Allowance, dated Jan. 28, 2015, issued in U.S. Appl. No. 14/295,059.
US Notice of Allowance (Corrected Notice of Allowability), dated Mar. 11, 2015, issued in U.S. Appl. No. 14/295,059.
US Office Action, dated Dec. 24, 2014, issued in U.S. Appl. No. 14/295,076.
US Final Office Action, dated Apr. 15, 2015, issued in U.S. Appl. No. 14/295,076.
US Office Action, dated Jul. 31, 2014, issued in U.S. Appl. No. 14/295,122.
US Notice of Allowance, dated Nov. 24, 2014, issued in U.S. Appl. No. 14/295,122.
US Notice of Allowance (Corrected Notice of Allowability), dated Jan. 5, 2015, issued in U.S. Appl. No. 14/295,122.
US Office Action, dated Mar. 14, 2014, issued in U.S. Appl. No. 14/154,009.
US Office Action, dated Sep. 29, 2014, issued in U.S. Appl. No. 14/154,009.
US Notice of Allowance, dated Jan. 21, 2015, issued in U.S. Appl. No. 14/154,009.
US Office Action, dated Nov. 25, 2014, issued in U.S. Appl. No. 14/154,019.
US Notice of Allowance, dated Mar. 20, 2015, issued in U.S. Appl. No. 14/154,019.
US Notice of Allowance (Corrected Notice of Allowability), dated May 14, 2015, issued U.S. Appl. No. 14/154,019.
US Office Action, dated Dec. 10, 2014, issued in U.S. Appl. No. 14/484,104.
US Notice of Allowance, dated Mar. 19, 2015, issued in U.S. Appl. No. 14/484,104.
US Notice of Allowance (Corrected Notice of Allowability), dated May 6, 2015, issued in U.S. Appl. No. 14/484,104.
US Office Action, dated Dec. 4, 2014, issued in U.S. Appl. No. 14/216,743.
US Final Office Action, dated Apr. 8, 2015, issued in U.S. Appl. No. 14/216,743.
US Office Action, dated Mar. 12, 2015, issued in U.S. Appl. No. 14/481,020.
US Final Office Action, dated Jul. 7, 2015, issued in U.S. Appl. No. 14/481,020.
US Office Action, dated Aug. 22, 2014, issued in U.S. Appl. No. 14/250,256.
US Final Office Action, dated Nov. 21, 2014, issued in U.S. Appl. No. 14/250,256.
US Office Action, dated Jul. 8, 2015, issued in U.S. Appl. No. 14/250,256.

US Office Action, dated Oct. 7, 2014, issued in U.S. Appl. No. 14/481,762.
US Final Office Action, dated Dec. 19, 2014, issued in U.S. Appl. No. 14/481,762.
US Office Action, dated Jul. 7, 2015, issued in U.S. Appl. No. 14/481,762.
Chinese First Office Action (no translation) dated Aug. 7, 2015 issued in CN 201410243180.6.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior.html], 10 pp.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.
Cooper, Daniel (Aug. 16, 2013) *Withings Pulse review*, http://www.engadget.com/2013/08/16/withings-pulse-revew/, 8 pages.
DesMarais, Christina (posted on Sep. 3, 2013) "Which New Activity Tracker is Best for You?" *Health and Home, Health & Fitness , Guides & Reviews*, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch With Wireless Sync," (Mar. 2009), Garmin Ltd., 56 pp.
Forerunner® 110 Owner's Manual, (2010) "GPS-Enabled Sport Watch," Garmin Ltd., 16 pp.
Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch with Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch with Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Larklife, User Manual, (2012) *Lark Technologies*, 7 pp.
Lark/Larkpro, User Manual, (2012) "What's in the box," *Lark Technologies*, 7 pp.
LIFETRNR, User Manual (2003, specific date unknown), NB new balance®, Implus Footcare, LLC, 3 pages.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, *Manufactured by Polar Electro Oy*, 11 pages.
Rainmaker, (Jun. 25, 2012, updated Feb 16, 2013) "Garmin Swim watch In-Depth Review," [retrieved on Sep. 9, 2013 at http://www.dcrainmaker.com/2012/06/garmin-swim-in-depth-review.html, 38 pp.

(56) References Cited

OTHER PUBLICATIONS

Rainmaker, (Jul. 25, 2013) "Basis B$_1$ Watch In-Depth Review," [retrieved on Feb. 4, 2014 at http://www.dcrainmaker.com/2013/07/basis-b1-review.html], 56 pp.

"Withings pulse, Quick Installation Guide" (Jul. 24, 2013) Withings Pulse QIG, v 1.3, withings.com/pulse, 16 pages.

Zijlstra, Wiebren, (2004) "Assessment of spatio-temporal parameters during unconstrained walking," *Eur J Appl Physiol*, 92:39-44.

Duun et al., "A Novel Ring Shaped Photodiode for Reflectance Pulse Oximetry in Wireless Applications," IEEE Sensors Conference 2007, 4 pp.

U.S. Appl. No. 14/954,753, filed Nov. 30, 2015, Richards et al.

US Notice of Allowance (Corrected Notice of Allowability), dated Dec. 18, 2015, issued in U.S. Appl. No. 14/507,184.

US Notice of Allowance, dated Nov. 25, 2015, issued in U.S. Appl. No. 14/673,630.

US Final Office Action, dated Nov. 4, 2015, issued in U.S. Appl. No. 14/673,634.

US Office Action, dated Oct. 22, 2015, issued in U.S. Appl. No. 14/295,076.

US Office Action, dated Oct. 2, 2015, issued in U.S. Appl. No. 14/216,743.

US Final Office Action, dated Feb. 8, 2016, issued in U.S. Appl. No. 14/216,743.

US Office Action, dated Oct. 27, 2015, issued in U.S. Appl. No. 14/481,020.

US Final Office Action, dated Oct. 23, 2015, issued in U.S. Appl. No. 14/250,256.

US Final Office Action, dated Nov. 5, 2015, issued in U.S. Appl. No. 14/481,762.

Litigation Document—"Complaint for Patent Infringement," filed Oct. 29, 2015, in U.S. District Court of Delaware [Re: U.S. Pat. No. 8,868,377, 8,920,332, and 9,089,760].

Litigation Document—"Report on the Filing or Determination of an Action Regarding a Patent or Trademark," filed Oct. 29, 2015, in U.S. District Court of Delaware [Re: U.S. Pat. No. 8,868,377, 8,920,332, and 9,089,760].

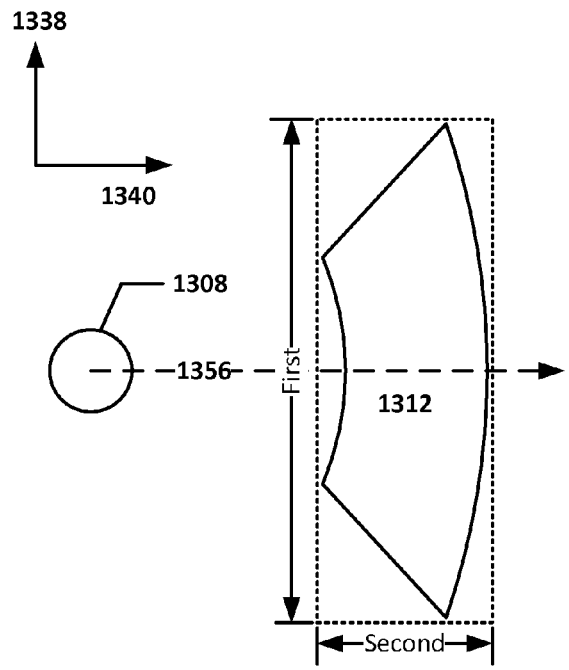
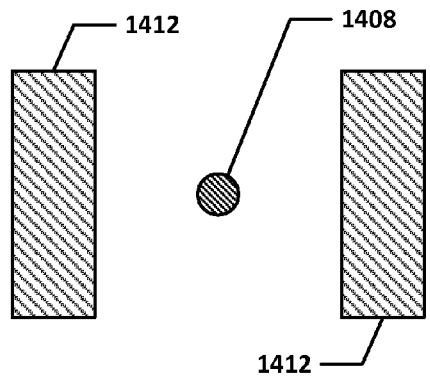
FIG. 13  FIG. 14
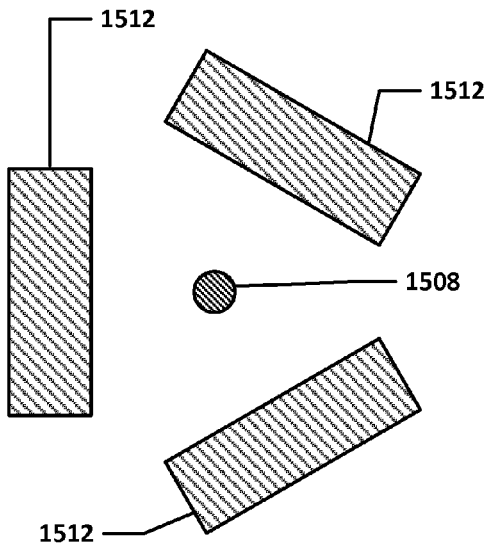
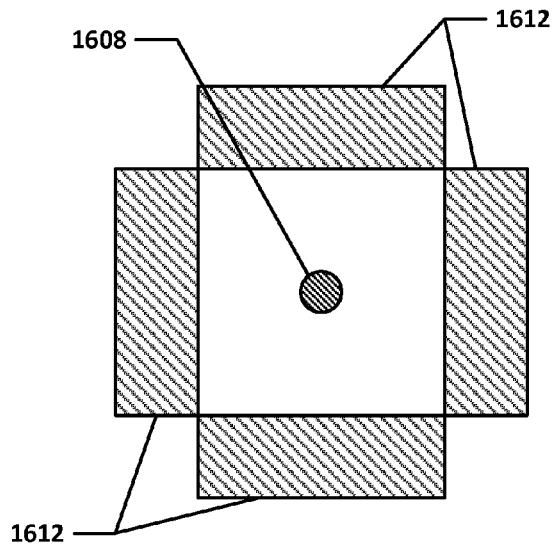
FIG. 15  FIG. 16

HEART RATE SENSOR WITH HIGH-ASPECT-RATIO PHOTODETECTOR ELEMENT

BACKGROUND

Heart rate may be measured using any of a variety of different sensors, including, for example, electrode-based sensors, such as EKG sensors, and optical sensors, such as photoplethysmographic (PPG) sensors. PPG sensors typically include a light source and a photodetector that are placed adjacent to a person's skin. The light source and photodetector are typically arranged so that light from the light source cannot reach the photodetector directly. However, when the PPG sensor is placed adjacent to a person's skin, light from the light source may diffuse into the person's flesh and then be emitted back out of the person's flesh such that the photodetector can detect it. The amount of such light that is emitted from the person's flesh may vary as a function of heart rate, since the amount of blood present in the flesh varies as a function of heart rate and the amount of light that is emitted from the person's flesh, in turn, varies as a function of the amount of blood present.

The assignee of this application, Fitbit, Inc., makes wearable fitness monitoring devices, some of which, such as the Charge HR™ and the Surge™, incorporate PPG sensors that include two high-brightness, green light-emitting diodes (LEDs) that are spaced approximately 8 mm apart, as well as a 2 mm square photodetector element located midway between the LEDs. Various other companies that make wearable fitness monitoring devices utilize a similar architecture. For example, the Basis Peak™ incorporates two green LEDs with a square photodetector element located midway between them, as does the Motorola Moto 360™.

FIG. 1 depicts a simplified representation of a prior-art wristband-type wearable fitness monitor 100 that incorporates a PPG sensor. The wearable fitness monitor 100, in this example, includes a housing 104 with two straps 102 attached; the straps 102 may be used to fasten the housing 104 to a person's forearm, in much the same manner as a watch (indeed, many such devices may incorporate timekeeping functionality as well). The PPG sensor, in this example, includes two light sources 108, with a photodetector element 112 interposed midway between them on a back face 128 of the housing 104; the photodetector element 112 in this example has a photosensitive area with a square aspect ratio. When the wearable fitness monitor 100 is worn by a person in a manner similar to a wristwatch, the back face 128 may be pressed against the person's skin, allowing the light sources 108 to illuminate the person's skin. The photodetector element 112 may then measure the amount of that light that is then emanated back out of the person's skin. Control logic (not pictured) within the housing 104 may then calculate the person's heart rate based on fluctuations in the amount of light measured by the photodetector element 112.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an apparatus having a light source and one or more discrete photodetector elements may be provided. Each photodetector element may have a first edge having a first length and may also have a first width in a direction perpendicular to the first edge. The apparatus may also include control logic, which may be communicatively connected with the light source and each photodetector element and configured to cause the light source to emit light, obtain one or more measured light intensity measurements from the one or more photodetector elements, and determine a heart rate measurement based, at least in part, on the one or more light intensity measurements. In such implementations, the ratio of the first length to the first width of each photodetector may be substantially between 2:1 to 5:1.

In some such implementations, the first edge of each photodetector element may be perpendicular or transverse to an axis radiating out from a center of the light source.

In some implementations of the apparatus, the light source may include a plurality of light-emitting devices.

In some such implementations, the plurality of light-emitting devices may include at least two light-emitting devices that predominantly emit light of different wavelengths. In some further or alternative such implementations, there may be a plurality of photodetector elements arranged in a pattern, and the plurality of light-emitting devices may be collocated at a center point of the pattern of photodetector elements. In some such implementations, each photodetector element in the pattern may be equidistant from the center of the light source and/or evenly spaced within the pattern.

In some implementations of the apparatus, the ratio of the first length to the first width of each photodetector element may be substantially between 2:1 to 3.5:1. In some other implementations of the apparatus, the ratio of the first length to the first width of each photodetector element may be substantially between 3.5:1 to 5:1.

In some implementations of the apparatus, each photodetector element may have a first length between 1 mm and 5 mm and a first width between 0.5 mm and 2 mm, with the ratio of the first length to the first width substantially between 2:1 to 5:1, and each such photodetector element may be positioned such that an edge of the photodetector element closest to the light source is between 1 mm and 4 mm from the light source.

In some implementations of the apparatus, there may be a pattern of photodetector elements that includes three or four photodetector elements that are equidistantly spaced about the light source.

In some implementations of the apparatus, the apparatus may also include a housing having a back face that includes one or more transparent window regions through which light may enter the apparatus. In such implementations, each photodetector element is positioned such that that photodetector element is overlapped by a corresponding one of the one or more transparent window regions, and the housing may be configured such that the back face is adjacent to the skin of a person wearing the apparatus when the apparatus is worn by that person.

In some such implementations of the apparatus, the back face may include a thin window, and the window regions may be sub-regions of the window that are defined by the photodetector elements. In some other or additional such implementations, each photodetector element may be offset from the corresponding transparent window region by a corresponding gap in a direction normal to the photodetector element, and the gap may be free of optical light guides.

In some implementations of the apparatus, each photodetector element may, in addition to the first edge, have an arcuate second edge opposite the first edge. The arcuate second edge may have a maximum distance from the first edge, when measured along a direction perpendicular to the first edge, that is equal to the first width.

In some implementations, an apparatus may be provided that includes a first light source and a second light source, as well as a photodetector element interposed between the first light source and the second light source. The apparatus may also include control logic that is communicatively connected with the first and second light sources and the photodetector element and that is configured to cause the first light source and the second light source to emit light, obtain measured light intensity measurements from the photodetector element, and determine a heart rate measurement based, at least in part, on the light intensity measurements. In such implementations, the photodetector element may be rectangular in shape, have a first edge with a first length, and have a second edge, perpendicular to the first edge, with a second length. Furthermore, in such implementations, the ratio of the first length to the second length may be substantially between 2:1 to 5:1.

In some such implementations, the first edge of each photodetector element may be perpendicular or transverse to an axis spanning between a center of the first light source and a center of the second light source.

In some other or additional such implementations, the apparatus may include a housing having a back face that includes a transparent window region that overlaps the photodetector element and two further window regions that are each associated with a different one of the first light source and the second light source and that allow light from the associated light source to pass through the back face. In such implementations, the first light source and the second light source may be the only light sources in the apparatus configured to emit light through the back face, and the housing may be configured such that the back face is adjacent to the skin of a person wearing the apparatus when the apparatus is worn by that person.

In some implementations of the apparatus, the photodetector element may be equidistant from the first light source and the second light source.

In some implementations, an apparatus may be provided that includes a light source and one or more photodetectors, each photodetector having a photosensitive area. In such implementations, at least 90% of the photosensitive area of the photodetector is defined by a first dimension along a first axis and a second dimension along a second axis perpendicular to the first axis. The apparatus may also, in such implementations, include control logic that is communicatively connected with the light source and each photodetector and that is configured to cause the light source to emit light, obtain one or more measured light intensity measurements from the one or more photodetectors, and determine a heart rate measurement based, at least in part, on the one or more light intensity measurements. In such implementations, the ratio of the first dimension to the second dimension may be substantially between 2:1 to 5:1.

In some implementations of the apparatus, the light source may include a plurality of light-emitting devices. In some such implementations, the plurality of light-emitting devices may include at least two light-emitting devices that predominantly emit light of different wavelengths. In some further or alternative such implementations, there may be a plurality of photodetector elements arranged in a pattern, and the plurality of light-emitting devices may be collocated at a center point of the pattern of photodetector elements. In some such implementations, each photodetector element in the pattern may be equidistant from the center of the light source and/or evenly spaced within the pattern.

In some implementations of the apparatus, the ratio of the first length to the first width of each photodetector element may be substantially between 2:1 to 3.5:1. In some other implementations of the apparatus, the ratio of the first length to the first width of each photodetector element may be substantially between 3.5:1 to 5:1.

In some implementations of the apparatus, each photodetector element may have a first length between 1 mm and 5 mm and a first width between 0.5 mm and 2 mm, with the ratio of the first length to the first width substantially between 2:1 to 5:1, and each such photodetector element may be positioned such that an edge of the photodetector element closest to the light source is between 1 mm and 4 mm from the light source.

In some implementations of the apparatus, there may be a pattern of photodetector elements that includes three or four photodetector elements that are equidistantly spaced about the light source.

In some implementations of the apparatus, the apparatus may also include a housing having a back face that includes one or more transparent window regions through which light may enter the apparatus. In such implementations, each photodetector element is positioned such that that photodetector element is overlapped by a corresponding one of the one or more transparent window regions, and the housing may be configured such that the back face is adjacent to the skin of a person wearing the apparatus when the apparatus is worn by that person.

In some such implementations of the apparatus, the back face may include a thin window, and the window regions may be sub-regions of the window that are defined by the photodetector elements. In some other or additional such implementations, each photodetector element may be offset from the corresponding transparent window region by a corresponding gap in a direction normal to the photodetector element, and the gap may be free of optical light guides.

In some implementations, an apparatus may be provided that includes a light source and at least one photodetector element. The apparatus may also include control logic that is communicatively connected with the light source and the photodetector element and that is configured to cause the light source to emit light, obtain at least one measured light intensity measurement from the at least one photodetector element, and determine a heart rate measurement based, at least in part, on the at least one light intensity measurement. In such implementations, the at least one photodetector element may subtend an angle at the center of the light source of substantially at least: $2 \cdot \arctan$ $$\left(\frac{1}{r_i}\right)$$

radians, where $r_i$ is a measurement of a distance from the center of the light source to the photodetector element, at least 80% of the photodetector element covers an annular region centered on the center of the light source and defined by $r_i$ and $r_o$, and $r_o$ is greater than $r_i$ by not more than 2 millimeters.

In some such implementations, the angle at the center of the light source subtended by the at least one photodetector element may be substantially at most: $2 \cdot \arctan$ $$\left(\frac{2.5}{r_i}\right)$$

radians.

In some implementations, an apparatus may be provided that includes a light source configured to emit light predominantly having wavelengths in the 500 nm to 600 nm range, as well as a photodetector element having a central opening. The apparatus may also include control logic that is communicatively connected with the light source and the photodetector element and that is configured to cause the light source to emit light, obtain measured light intensity measurements from the photodetector element, and determine a heart rate measurement based, at least in part, on the light intensity measurements. In such implementations, the light source may be positioned so as to emit light through the central opening of the photodetector element, and the photodetector element may have a) an exterior periphery defined by a first boundary and b) a second boundary defining the central opening.

In some such implementations, the first boundary and the second boundary may form an annulus, the first boundary may be radially offset from the second boundary by a first distance, and the ratio of the circumference of the second boundary to the first distance may be between 9.5:1 to 11.5:1.

In some other or additional such implementations, the first boundary and the second boundary may form an annulus, the first boundary may have a diameter of between 3 to 5.5 mm, and the second boundary may have a diameter of between 1 to 2.5 mm.

In some implementations of the apparatus, the second boundary may be a regular polygon of N sides each having a second length, and for each of the N sides of the second boundary, the first boundary may be offset from that side of the second boundary by a first distance along a reference axis that originates at a center of the light source and passes through the midpoint of that side of the second boundary. In such implementations, the ratio of the second length to the first distance for each of the N sides may be between 2:1 to 5:1.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 13 depicts a diagram of a HAR photodetector element that is arcuate in shape, in accordance with an example implementation.

FIGS. 14 through 17 depict several examples of implementations with multiple HAR photodetectors, in accordance with several example implementations.

FIG. 18 depicts an example of a PPG sensor photodetector layout as shown in FIG. 15 but with multiple light-emitting devices used in the light source, in accordance with an example implementation.

DETAILED DESCRIPTION

The present disclosure relates to PPG sensors and, more particularly, to PPG sensors designed for use with wearable biometric monitoring devices (also referred to herein as "biometric tracking devices," "biometric tracking modules," "wearable fitness monitors," or the like). The present inventors have determined that the use of non-square photodetector elements in PPG sensors may provide a significant performance increase as compared with traditional PPG designs, which typically utilize square photodetector elements. The present inventors have also determined that such a performance increase may be obtained, if desired, while still maintaining essentially the same power consumption as a square photodetector element in a traditional PPG design.

Figures 1, 2:
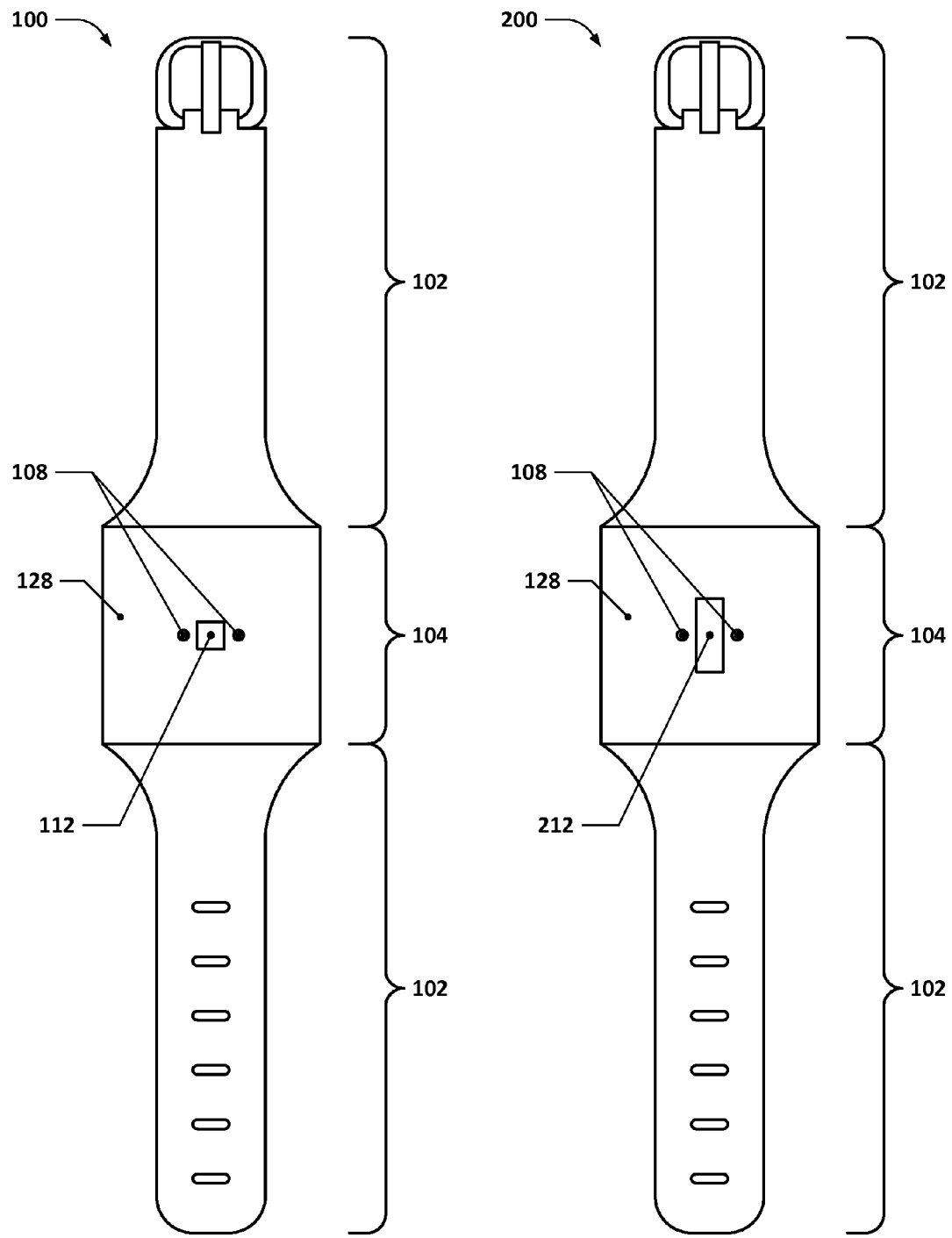
FIG. 1 depicts a simplified representation of a prior-art wristband-type wearable fitness monitor that incorporates a PPG sensor.
FIG. 2 depicts a simplified representation of a wristband-type wearable fitness monitor that incorporates a PPG sensor that uses a non-square photodetector element, in accordance with an example implementation.

FIG. 2 depicts a simplified representation of a wristband-type wearable fitness monitor 200 that incorporates a PPG sensor that uses a non-square photodetector element in accordance with an example implementation of the concepts arrived at by the present inventors and discussed below. The wearable fitness monitor 200, in this example, shares many components in common with the prior art wearable fitness monitor 100, including the control logic, the housing 104 and the straps 102, the back face 128, and the two light sources 108. The wearable fitness monitor 200, however, features a photodetector element 212 which has a non-square active area in place of the photodetector element 112.

As discussed above, PPG sensors operate by shining light into a person's skin. This light diffuses through the person's flesh and a portion of this light is then emitted back out of the person's skin in close proximity to where the light was introduced into the flesh; the amount of light that is emitted back out of the person's flesh attenuates with increasing distance from the light source. This effect can be seen when one holds a bright penlight or other concentrated light source against one's skin; the flesh surrounding the area where the light source contacts the skin will glow red or orange from the diffused light. While imperceptible to the human eye, the amount of this light that is emanated from the person's skin will fluctuate in sync with the person's heart rate. As a person's heart beats, the person's blood vessels expand and contract in synch with the heart as the pumping of the heart exerts pressure on the person's blood which, in turn, results in cyclic pressure increases in the person's blood vessels. When a blood vessel expands, it allows more blood to flow into the vessel, which results in the amount of blood present in a given region of the person's flesh fluctuating in rhythm with the person's heart rate. This, in turn, results in fluctuations in the amount of light from the light source that is emanated back out of the flesh. The heart rate may then be determined by measuring the amount of light that emanates back out of the person's flesh via the above-described diffusion mechanism. Such measured light may have two components—a component that remains constant, i.e., the light that generally emanates from the skin regardless of heart rate, and a component that fluctuates with heart rate. The light that remains constant may be referred to herein as "DC," as it may be thought of as analogous in some respects to direct current since it remains relative constant over time. The light that fluctuates may be referred to herein as "AC," as it may be thought of as analogous to alternating current since it fluctuates relatively regularly over time. A typical heart rate might range from 50 beats per minute (BPM) to 200 bpm, and the AC component of light may have a frequency that maps to the heart rate frequency.

Generally speaking, the AC component of the detected light, which may be referred to herein as "AC optical power" or, more generally, simply as "light intensity," may be much smaller in magnitude than the DC component, as a large amount of the light that is diffused into the person's skin and then emanated out will still emanate regardless of the changes in the amount of blood present due to the heart beating. However, the AC component is of principle interest since it is what is indicative of heart rate.

Figure 3:
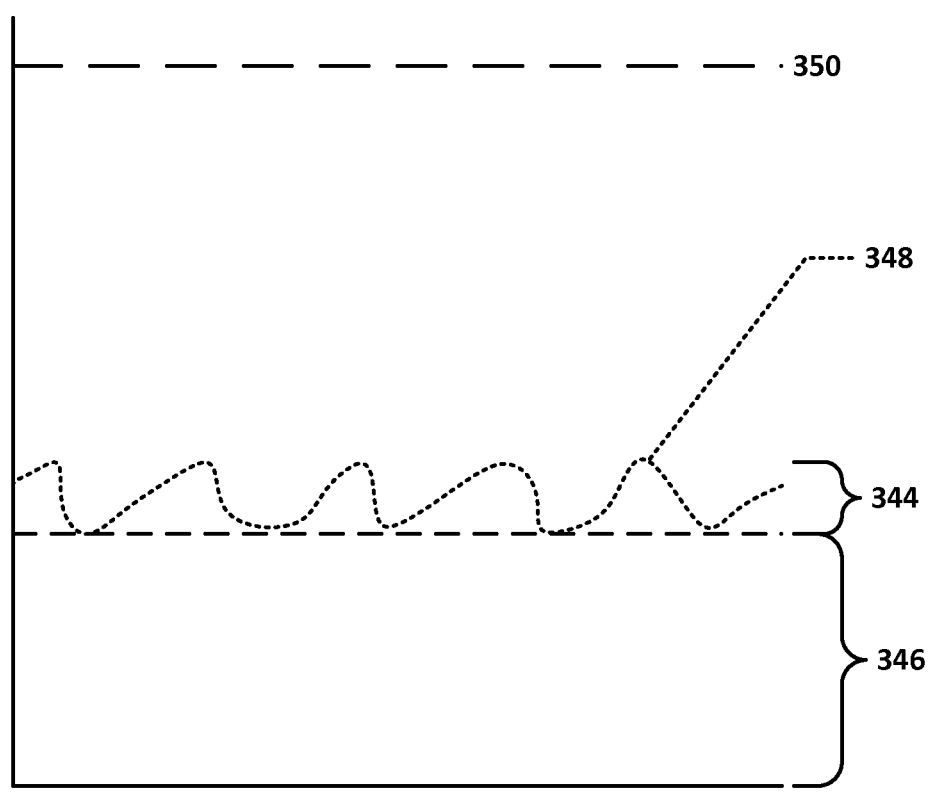
FIG. 3 is a theoretical plot of emitted light intensity and detected light intensity for an example PPG sensor that is used to obtain heart rate information from a person's flesh, in accordance with an example implementation.

FIG. 3 is a theoretical plot of emitted light intensity and detected light intensity for an example PPG sensor that is used to obtain heart rate information from a person's flesh, in accordance with an example implementation. It is to be understood that FIG. 3 is not to scale and does not depict actual data; it is merely intended to assist the reader in understanding the difference between the AC and DC components of a detected light signal. In FIG. 3, the horizontal axis indicates time, and the vertical axis indicates light intensity. As can be seen, light is emitted into the person's flesh at a constant value 350 in this example. Light emanating from the person's skin is then measured by a photodetector element; this measured light intensity is depicted as data trace 348. The data trace 348 may be split into a DC component 346, which does not fluctuate with time, and an AC component 344, which does fluctuate with time.

As noted above, a conventional PPG sensor may include a square photodetector element that is located near a light source (or, in many cases, near two or more light sources). The present inventors determined that such an arrangement was inefficient in terms of signal collection as a function of potential power consumption. For example, photodetectors are typically composed of a single photosensitive lateral area, e.g., the area of the photodetector that is parallel to the photodetector die top surface, that provides an output signal that indicates the total amount of light that is incident on the photosensitive cell at any given moment in time. The amount of power that such a photodetector consumes is directly tied to the size of the photosensitive area of the photodetector. The present inventors determined that, for a square photodetector element, a large percentage of the photodetector element may be located in positions where a much lower amount of AC light is emanated in comparison to locations where other portions of the photodetector element are located. This effect is discussed in more detail with respect to some of the Figures, as set forth below.

Figure 4:
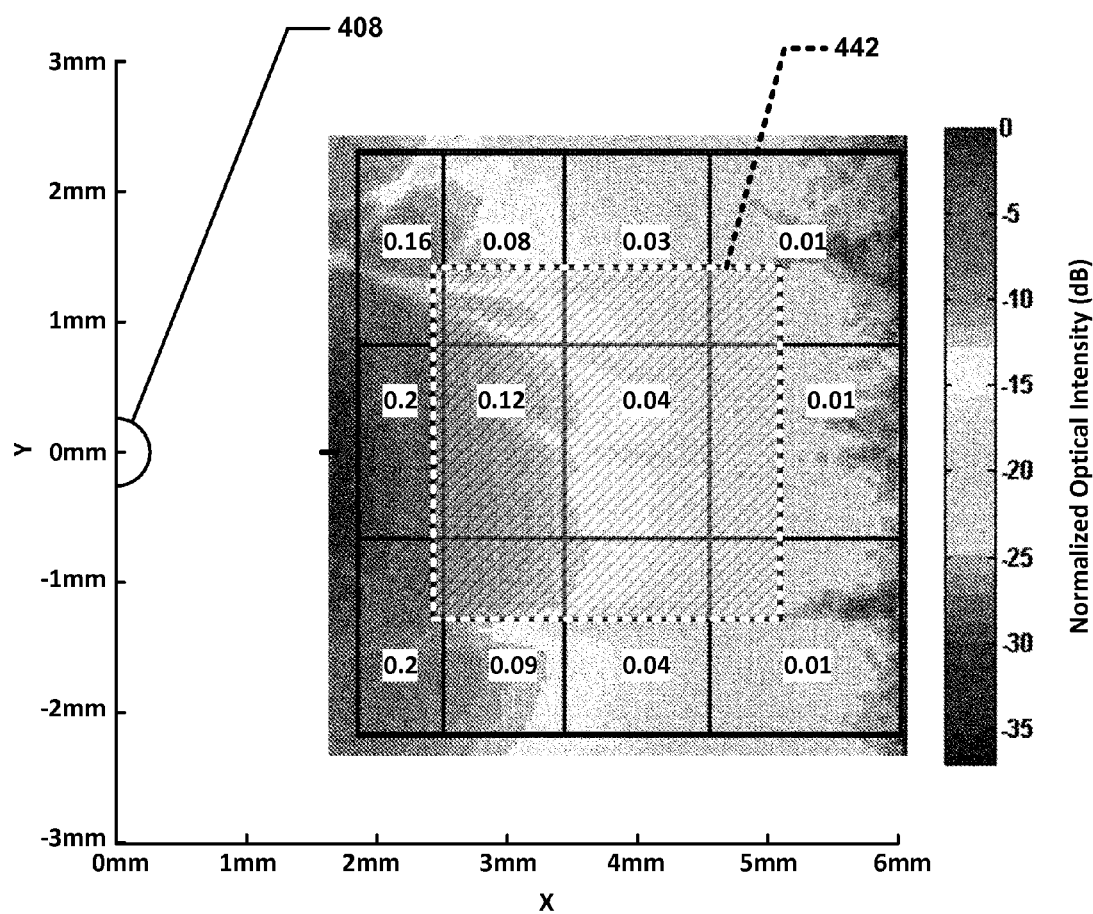
FIG. 4 depicts a grey-scale plot of measured AC power intensity for light emanated from a rectangular region measuring approximately 4.5 mm wide by 5 mm tall on a person's arm near the wrist, in accordance with an example implementation.

FIG. 4 depicts a grey-scale plot of measured AC power intensity for light emanated from a rectangular region measuring approximately 4.5 mm wide by 5 mm tall on a person's arm near the wrist, in accordance with an example implementation. A light source 408 is positioned at X=0 mm and Y=0 mm and shines light into the person's arm; the intensity of the light that is emanated back out is reflected in the shading in the image (the largest and smallest light intensities, due to the limitations of using black and white ink, appear similar—it is to be understood that the light intensity is greatest at the left side of the image and then falls off to the lowest intensities at the right edge of the image). The light source used in FIG. 4 was a 1.9 mm diameter green-wavelength LED, although the illumination beam that it produced was concentrated in an area smaller than that. FIG. 4 is based on actual image data taken with a human subject; as such, it includes various imperfections, such as hairs, that result in asymmetries in the light intensity detected. The light source that was used in this example emitted light that was predominantly in the 515 nm to 545 nm range, i.e., primarily green light.

The rectangular region has been divided into twelve rectangular bins; the number in each bin indicates the fraction of the overall AC light intensity (also referred to as the "power fraction") within the total bin area that is attributable to that particular bin. Thus, the bin in the lower left corner sees 20% of the total AC light intensity or power that is emitted from the totality of the twelve bins, whereas the bin immediately to the right of that bin only sees 9% of the total AC light intensity or power within that region.

FIG. 4 also depicts the footprint 442 of a typical, square photodetector element at a spacing of approximately 2.5 mm from the light source center. As used herein, the terms "photodetector element," "active area," "active region," "photosensitive area," and "footprint" (with respect to a photodetector) all refer to the same portion of a photodetector, namely, the area of the photodetector that can actually detect light that is incident on the photodetector. It is to be understood that photodetectors may also include other components that are outside of the active area, such as interconnects, circuits, application-specific integrated circuits (ASICs), etc. that interact with the photodetector element in order to provide power or produce signal output. These other components are not to be considered to be part of the photodetector element. Thus, a photodetector with a 2 mm by 2 mm square photodetector element having a 1 mm by 2 mm ASIC located adjacent to one edge of the photodetector element might have an overall size of 3 mm by 2 mm, which would be rectangular, but the photodetector element of that photodetector would not be rectangular since the ASIC is not part of the photodetector element. It is also to be understood that reference herein to a "square" photodetector refers to a photodetector that has a square photodetector element, regardless of the aspect ratio that the entire photodetector has. Similarly, reference herein to a "rectangular" or "non-square" photodetector is to be understood as referring to a photodetector with a rectangular or non-square, respectively, photodetector element, regardless of whether the photodetector overall has a square shape.

Due to the aspect ratio and positioning of the square photodetector element, more than half of the active area is only able to measure light from the rightmost six bins, which represent only 14% of the available AC power in the overall bin area. The square photodetector element will not even collect all of the available light from those rightmost six bins since it only fully overlaps one of those rightmost six bins— only part of the light emanated from the remaining five bins of the rightmost six bins will be collectable by the square photodetector element. As shown, the square photodetector element may only be able to measure about 20% of the available light intensity that is emitted across all twelve bins.

Even if the square photodetector element is shifted to the left so that the edge closest to the light source is located at approximately 1.85 mm from the light source center, approximately 40% of the square photodetector element will still only be able to measure light from the rightmost six bins. In this case, the square photodetector element may collect roughly 50% of the AC optical power available in the 12 bins.

The present inventors have determined that a significant performance increase may be realized by deviating from the typical square (or nearly-square) aspect ratios that are used in photodetector elements of conventional PPG sensors. More specifically, the present inventors have determined that using a high-aspect-ratio photodetector element may provide a significant improvement in the amount of AC light measurable by a photodetector without incurring a significant power consumption penalty as compared with square photodetectors of the same active area. As used herein, the term "high-aspect-ratio" (or "HAR") photodetector refers to non-square photodetectors where at least 90% of the photodetector element active area, which may be referred to herein as the "active area of interest," has a maximum first dimension along a first axis that is at least twice as large as a maximum second dimension of the photodetector element along a second axis that is perpendicular or orthogonal to the first axis; the second axis is parallel to a ray emanating from the center of a light source used with the photodetector to form a PPG sensor, and the first axis is perpendicular to that ray. The maximum first dimension may be thought of as the distance between two lines that are both parallel to the ray emanating from the center of the light source and that pass through the opposing ends of the active area of interest that are furthest from the ray in directions perpendicular to the ray. The maximum second dimension, correspondingly, may be thought of as the distance between two lines that are both perpendicular to the ray emanating from the center of the light source and that pass through the opposing ends of the active area of interest that are furthest from and closest to the center of the light source. The "maximum first dimension" may also be referred to herein and in the claims as the "height" or "length" of a HAR photodetector, and the "maximum second dimension" may also be referred to herein and in the claims as the "base" or "width" of a HAR photodetector.

It is to be understood that while the examples discussed herein feature HAR photodetector elements with long axes that are perpendicular to rays extending out from a PPG sensor light source, similar performance benefits may be realized by utilizing similarly-sized photodetector elements that are not strictly perpendicular, e.g., ±10° from perpendicular. More generally, the concepts discussed herein may be practiced using HAR photodetector elements that are arranged with the long axis of such HAR photodetector elements being transverse to rays radiating outwards from the center of the light source.

Figure 5:
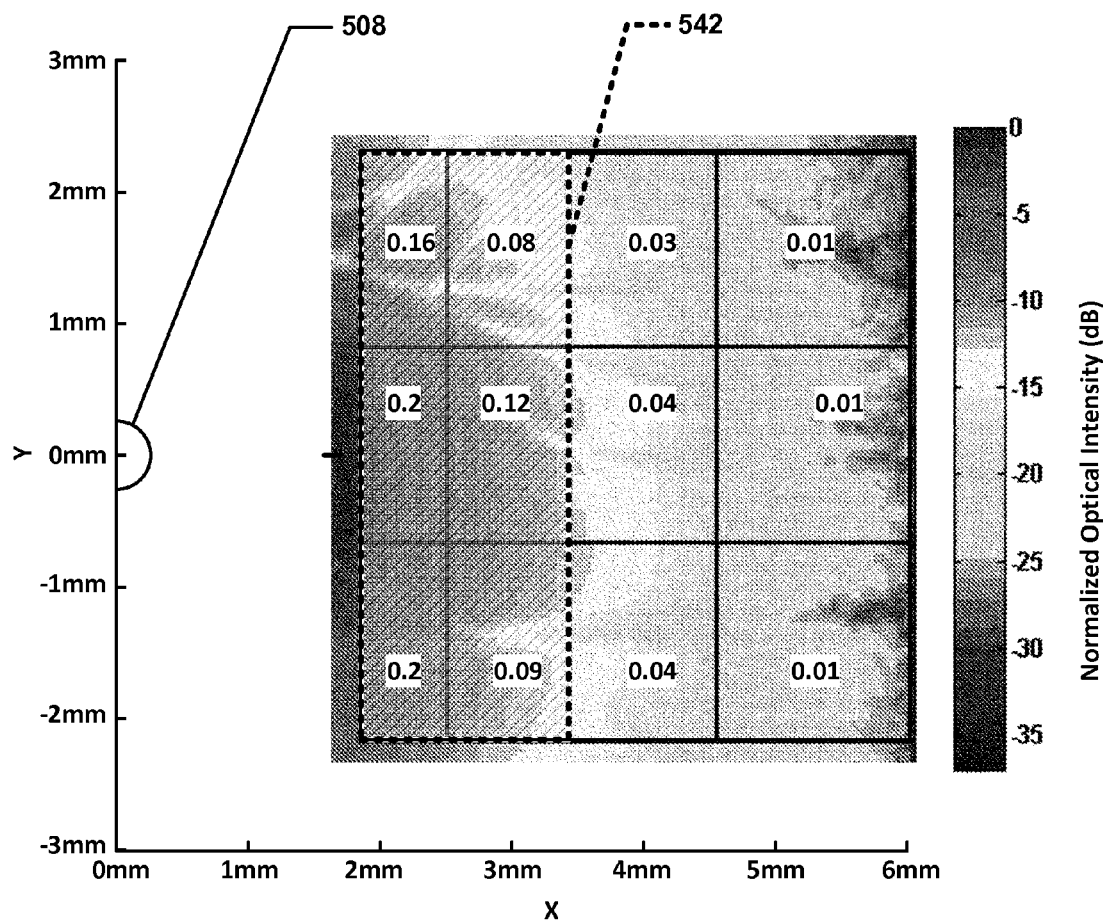
FIG. 5 depicts the same light intensity image map of FIG. 4, but with the outline of a high-aspect-ratio photodetector element added to the Figure, in accordance with an example implementation.

FIG. 5 depicts the same light intensity image map of FIG. 4, but with the outline of a high-aspect-ratio photodetector element added to the Figure, in accordance with an example implementation. The HAR photodetector element outline that is shown has a height-to-width aspect ratio of approximately 2.8 to 1, and completely overlaps with the leftmost six bins, which represent nearly 85% of the available AC power in the overall bin area. Thus, the HAR photodetector element shown in FIG. 5 is able to collect nearly four times as much light as the square photodetector element shown in FIG. 4. The HAR photodetector is able to offer such improved light collection capabilities while still having substantially the same active area as the square photodetector of FIG. 4. For example, a square photodetector element may have an active area of approximately 7 $mm^2$ and a HAR photodetector element may have an active area of approximately 7 $mm^2$. As a result, the power consumed by both the square photodetector and the HAR photodetector will be approximately equal since they have the same active area. Thus, the HAR photodetector in the example simulation shown in FIG. 5 offers a 300% improvement in collected AC power as compared with a traditional square photodetector implementation as set forth in FIG. 4, while requiring effectively no additional power in order to attain such an improvement.

Figure 6:
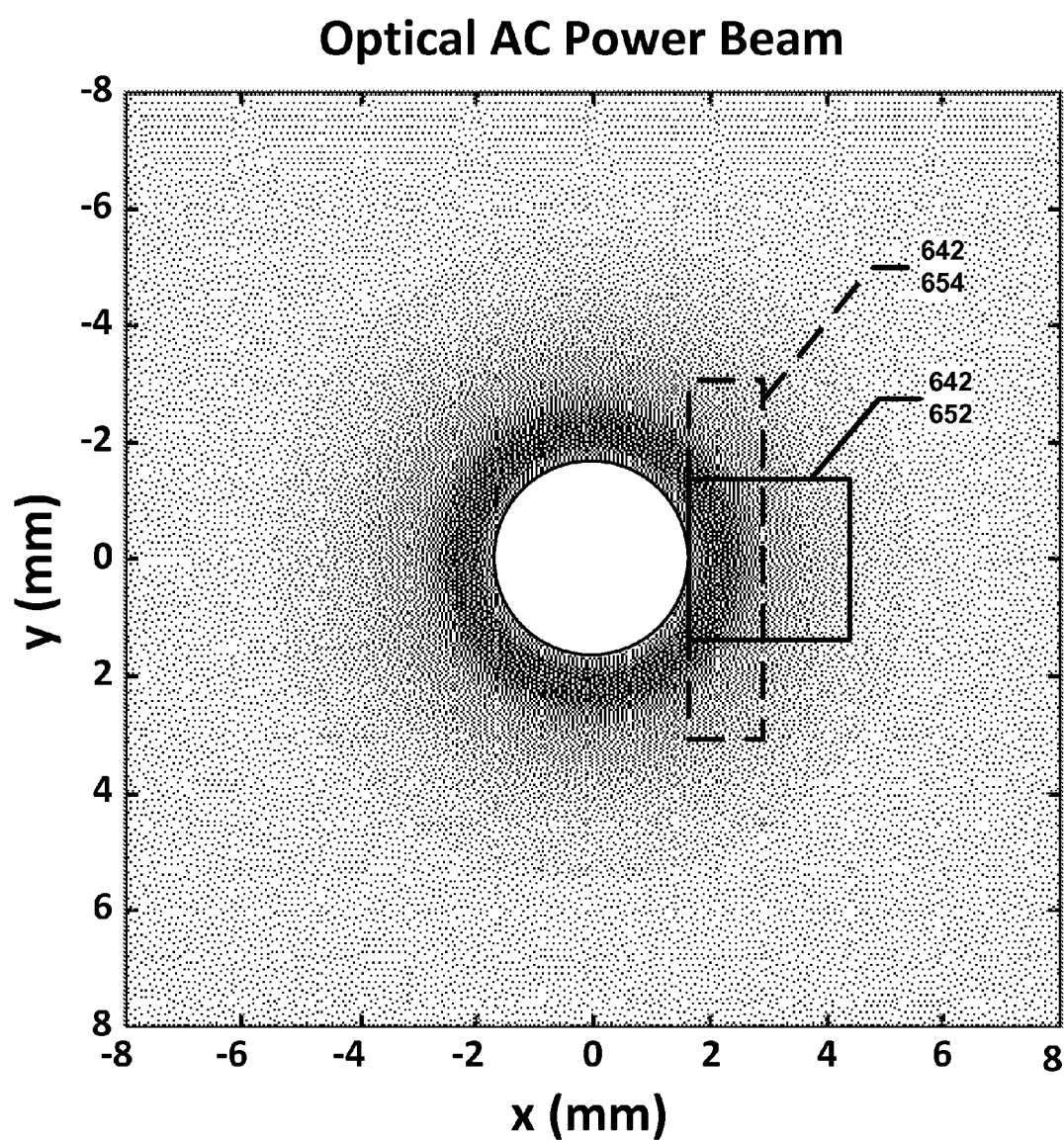
FIG. 6 depicts a simulation of the AC intensity or power of light that is emanated within a 16 mm by 16 mm region of skin as a result of light that is shined into the skin at the center of the region, in accordance with an example implementation.

FIG. 6 depicts a simulation of the AC intensity or power of light that is emanated within a 16 mm by 16 mm region of skin as a result of light that is shined into the skin at the center of the region, in accordance with an example implementation. In FIG. 6, there are two photodetector active area footprints 642 shown—one for a square photodetector footprint 652 and one for a HAR photodetector footprint 654. Both have areas of 7.5 $mm^2$, which is the area of the photosensitive area of the square photodetector used in the Fitbit Charge HR™ and Surge™ products, and are positioned with the edge closest to the light source offset from the light source center by 1.65 mm. The stippling density in FIG. 6 provides an indication of relative intensity—the higher the stippling density, the higher the light intensity (the center region is not stippled since this area is, in effect, the region through which light is introduced into the skin, plus some buffer, and it is unsuitable for obtaining light intensity measurements). As can be seen, a much higher proportion the HAR photodetector footprint 654 overlaps with higher-density stippling/light intensity regions than is the case with the square photodetector footprint 652.

Figure 7:
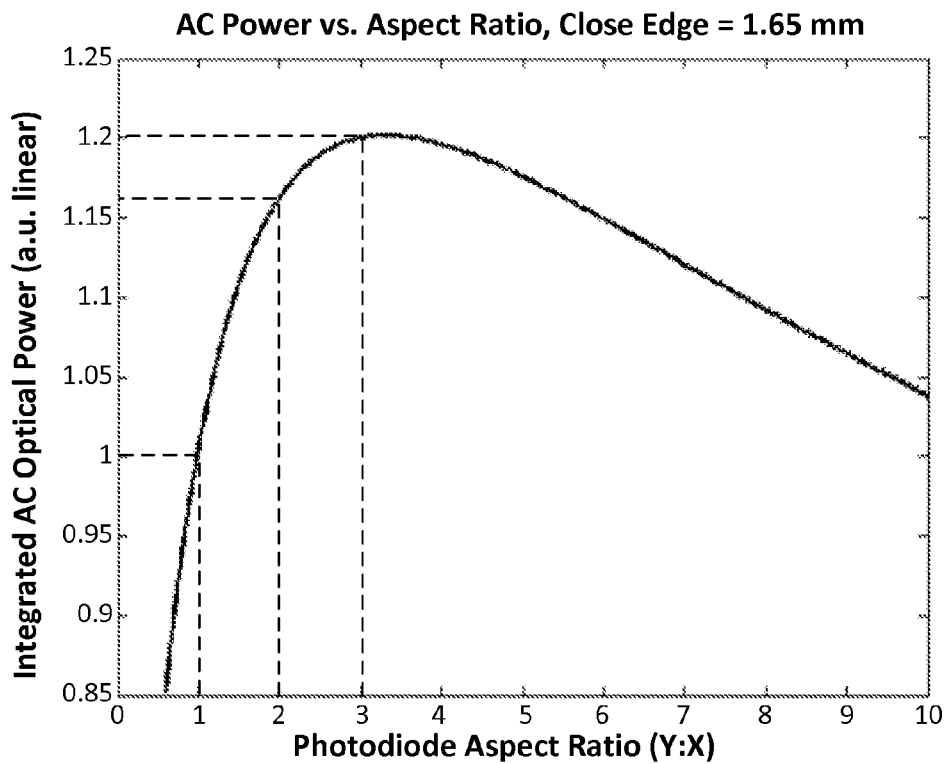
FIG. 7 depicts a plot of measurable AC light power as a function of photodetector footprint aspect ratio with regard to the simulation shown in FIG. 6, in accordance with an example implementation.

FIG. 7 depicts a plot of measurable AC light power as a function of photodetector footprint aspect ratio with regard to the simulation shown in FIG. 6, in accordance with an example implementation. The vertical axis represents the AC light power that is measurable by the photodetector, and the horizontal axis represents the aspect ratio of the photodetector; the vertical axis has been normalized such that a 1:1 aspect ratio photodetector provides a measurable AC light power value of 1. As can be seen, by utilizing a HAR photodetector, such as a photodetector with an aspect ratio of 2:1 or 3:1, the amount of AC light that is measurable by the HAR photodetector may be increased by up to 20% as compared with the square photodetector. This is a lower performance increase than was discussed above with respect to FIG. 5, but is still significant in terms of power consumption efficiency of a PPG sensor. In the modeled scenario, a HAR photodetector with an aspect ratio of between 3:1 and 4:1 provides the highest performance in this respect. As used herein, the term "between," with reference to a range, is used to indicate a range that is inclusive of the upper and lower limits of the range. Thus, in the above example, aspect ratios of 3:1 and 4:1 would be included in the range of "between 3:1 and 4:1." This convention is used throughout this paper and in the claims. The same observation may be made with respect to the use of "to" to describe an implied range, e.g., "a ratio of 3:1 to 4:1" would mean "between 3:1 to 4:1" and 3:1 and 4:1 would be included in this range.

Figure 8:
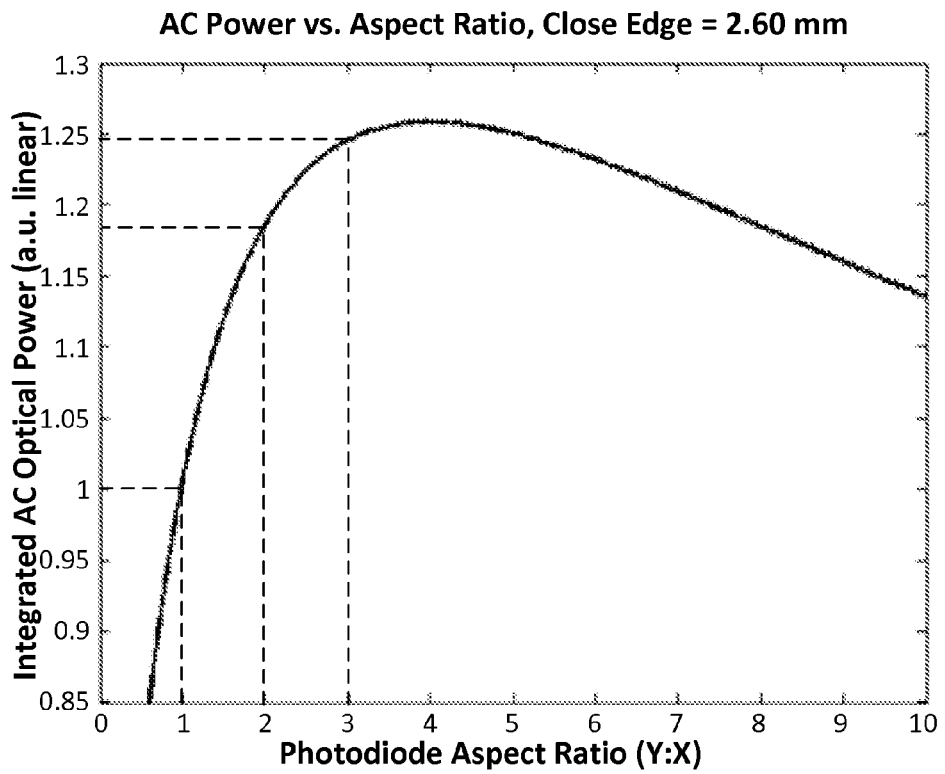
FIG. 8 depicts a plot of measurable AC light power as a function of photodetector footprint aspect ratio with regard to the simulation shown in FIG. 6, but with the edge of the photodetector closest to the center of the light source offset from the light source center by 2.6 mm instead of 1.65 mm, in accordance with an example implementation.

FIG. 8 depicts a plot of measurable AC light power as a function of photodetector footprint aspect ratio with regard to the simulation shown in FIG. 6, but with the edge of the photodetector closest to the center of the light source offset from the light source center by 2.6 mm instead of 1.65 mm, in accordance with an example implementation. The vertical axis represents the AC light power that is measurable by the photodetector, and the horizontal axis represents the aspect ratio of the photodetector; the vertical axis has been normalized such that a 1:1 aspect ratio photodetector provides a measurable AC light power value of 1. As can be seen, a similar performance increase can be observed when using a HAR photodetector even at the increased spacing from the light source, although the performance increase is slightly more pronounced, e.g., up to ~27% for HAR photodetectors with aspect ratios of 3:1 to 5:1.

In view of the above, in some implementations, a PPG sensor may utilize one or more HAR photodetector elements having aspect ratios of between 2:1 and 5:1. In some implementations, a PPG sensor may utilize one or more HAR photodetector elements having ratios of between 2:1 and 7:2, and in some other implementations, a PPG sensor may utilize one or more HAR photodetector elements having ratios of between 7:2 to 5:1. It is to be understood that HAR photodetector elements may have proportions that fall substantially between the aspect ratios discussed herein, both prior to and after this point, e.g., HAR photodetector elements may also have dimensions within ±0.1 mm of dimensions that would satisfy such aspect ratios or have aspect ratios within ±10% of such aspect ratios, e.g., for a 2:1 to 5:1 aspect ratio range, HAR photodetector elements having aspect ratios of 1.8:1 or 5.5:1 may be considered as having aspect ratios substantially between aspect ratios between 2:1 and 5:1.

HAR photodetectors may have increased effectiveness when arranged and sized according to one or more guiding principles, as discussed in more detail below.

As mentioned earlier, at least 90% of the active or photosensitive area of a HAR photodetector may have a maximum first dimension along a first axis that is at least twice as large as a maximum second dimension of the active or photosensitive area along a second axis that is perpendicular or orthogonal to the first axis; the second axis is parallel to a ray emanating from the center of a light source used with the photodetector to form a PPG sensor, and the first axis is perpendicular to that ray. This concept is discussed in more detail below, with reference to several Figures.

Figure 9:
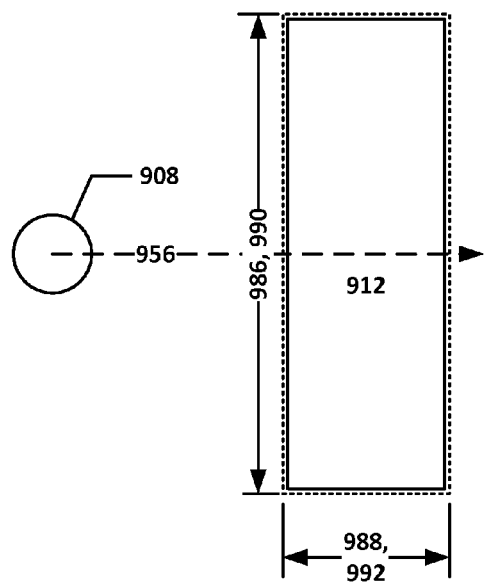
FIG. 9 depicts a diagram of a high-aspect-ratio ("HAR") photodetector element that is rectilinear, in accordance with an example implementation.

FIG. 9 depicts a diagram of a HAR photodetector element 912 that is rectilinear, in accordance with an example implementation. As can be seen, the active area of the HAR photodetector element 912 is rectangular and has a first dimension 986 along an axis that is perpendicular to a ray 956 emanating from the center of a light source 908, and a second dimension 988 along an axis that is parallel to the ray 956; the first dimension 986 and the second dimension 988 are thus orthogonal to one another. The HAR photodetector element 912, in this case, has a form factor where the active area as a whole has a first dimension 986 that is three times larger than the second dimension 988, i.e., 100% of the active or photosensitive area of the HAR photodetector element 912 has a maximum first dimension that is at least twice (in this case, thrice) as large as the maximum second dimension.

In this particular example, the HAR photodetector element 912 is a rectangular element, which is the most efficient shape in terms of manufacturing yield, as such photodetector elements may be made by simply dicing a semiconductor wafer with the requisite semiconductor elements for the photodetector elements in a rectangular grid, much in the same manner that square photodetector elements are manufactured (just with a different dicing spacing).

HAR photodetectors, as described herein, may also take on HAR shapes other than simple rectangles. Several examples of such alternative photodetector elements are discussed in more detail below.

Figure 10:
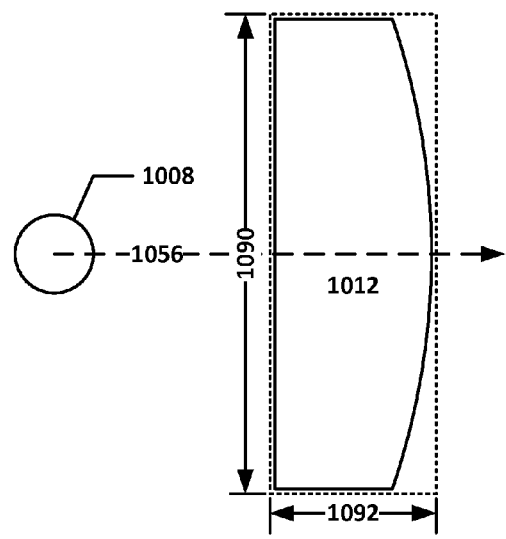
FIG. 10 depicts a diagram of a HAR photodetector element that is generally rectangular, but that possesses some non-rectangular aspects, in accordance with an example implementation.

FIG. 10 depicts a diagram of a HAR photodetector element 1012 that is generally rectangular, but that possesses some non-rectangular aspects, in accordance with an example implementation. The HAR photodetector element 1012 may have a first edge that is closest to the light source 1008, and an arcuate second edge that is opposite the first edge. If one considers the entire active area of the HAR photodetector element 1012, it is apparent that the HAR photodetector element 1012 has an active area with a maximum first dimension 1090 and a maximum second dimension 1092, which is the same as with the HAR photodetector element 912. Thus, the depicted HAR photodetector element 1012 would also be considered to have an aspect ratio of 3:1.

Figure 11:
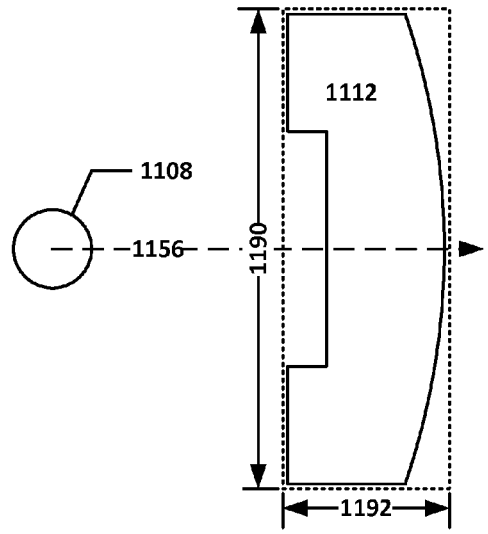
FIG. 11 depicts a diagram of a HAR photodetector element that is similar to the HAR photodetector element of FIG. 10, but with a rectangular cutout along the first edge, in accordance with an example implementation.

FIG. 11 depicts a diagram of a HAR photodetector element 1112 that is similar to the HAR photodetector element of FIG. 10, but with a rectangular cutout along the first edge, in accordance with an example implementation. While the active area of such a photodetector element differs from the photodetector elements of FIGS. 9 and 10, the HAR photodetector element 1112 active area still has a maximum first dimension 1190 that is three times larger than a maximum second dimension 1192 of the active area.

Figure 12:
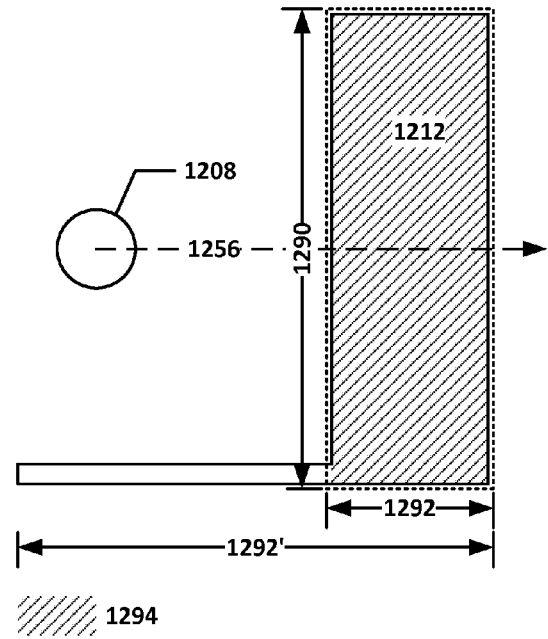
FIG. 12 depicts a diagram of a HAR photodetector element that is similar to the HAR photodetector element of FIG. 9, but one where the active area is generally rectangular yet has a "peninsula" that protrudes out from the rectangular area, in accordance with an example implementation.

FIG. 12 depicts a diagram of a HAR photodetector element 1212 that is similar to the HAR photodetector element of FIG. 9, but one where the active area is generally rectangular yet has a "peninsula" that protrudes out from the rectangular area, in accordance with an example implementation. In this case, if one considers 100% of the active area of the photodetector, the maximum first dimension 1290 and the maximum second dimension 1292' would technically be the same, which would result in an aspect ratio of 1:1. However, if the active area of the peninsula is omitted, the remaining 90% of the active area of the photodetector element 1212, e.g., active area of interest 1294, indicated by diagonal cross-hatching, has a maximum first dimension 1290 that is three times larger than the maximum second dimension 1292. Accordingly, such a photodetector element 1212 may be considered to be a HAR photodetector element under the conditions described herein.

FIG. 13 depicts a diagram of a HAR photodetector element 1312 that is arcuate in shape, in accordance with an example implementation. In this case, the HAR photodetector element 1312 has an active area with a maximum first dimension that is also three times larger than the maximum second dimension.

To be clear, all of the examples of photodetector elements shown in FIGS. 9 through 13 may be classified as HAR photodetector elements since at least 90% of the active or photosensitive area of each of these photodetector elements has a maximum first dimension along a first axis, where the first axis is perpendicular to a ray emanating from the center of the light source of a PPG sensor, that is at least twice as large as a maximum second dimension of the active or photosensitive area along a second axis that is perpendicular or orthogonal to the first axis. There are, of course, other shapes and examples of photodetector elements that may be considered to be HAR photodetector elements, commensurate with the above discussion.

Generally speaking, while only one light source and one photodetector element are needed in order to construct a PPG sensor, including multiple light sources or light-emitting devices and/or multiple photodetector elements may offer increased sensitivity, but at the expense of increased power consumption.

If multiple light-emitting devices are used, they may, for example, be spaced apart from one another, as shown in FIGS. 1 and 2, or may be closely grouped. In some implementations, all such light sources may be the same type of light source. In some other implementations, however, different types of light sources may be used for some or all of the light sources. For example, it may be desirable to utilize an LED that predominantly emits light in the green light spectrum for the purposes of detecting heart rate since the fluctuations in the light that is emitted back out of the person's skin may be more pronounced in the green light spectrum. At the same time, photoplethysmographic techniques may also be used to measure other physiological parameters besides heart rate, such as blood oxygenation levels. It may, in such situations, be desirable to utilize an LED that predominantly emits light in the red or infrared spectrum for such purposes. Thus, it may be desirable to include separate light-emitting devices that are each able to emit different wavelengths of light; each light-emitting device may be used to supply light for a different type of photoplethysmographic measurement. In some implementations, these light-emitting devices or light sources may be distributed across the PPG sensor face—for example, the light source 108 on the left side of FIG. 2 may be a green-wavelength LED, and the light source 108 on the right side of FIG. 2 may be a red- or infrared-wavelength LED. In some other implementations, light emitting devices may be closely clustered together, e.g., within a millimeter or two or less of each other; in such implementations, the clustered light-emitting devices may be viewed as a single light source with a center point that is, for example, associated with the centroid of the light intensity distribution of the cluster of light-emitting devices when all of the light-emitting devices in the cluster are emitting light simultaneously or that is associated with the averaged location of all of the light-emitting devices in the cluster. For light sources with single light-emitting devices, the center of the light source is to be understood as corresponding to a point generally associated with the centroid of the light intensity distribution of that light-emitting device, e.g., typically the center of the LED. It is to be understood that the term "light-emitting device," as used herein, refers to a single, discrete light-emitting device, such as a single LED or a laser diode, and that the term "light source," as used herein, refers to one or more light-emitting devices that are generally treated as a unit, e.g., that are close enough together that an observer would not be able to discern a gap between the light-emitting devices in a group of light-emitting devices when the light-emitting devices in the group are all emitting light simultaneously and the observer is approximately two to three feet from the light-emitting devices (this assumes that the light-emitting devices are emitting light in a spectrum visible to the observer; for light-emitting devices that emit light in a non-visible spectrum, e.g., infrared, such an evaluation may be based on whether gaps between such light-emitting devices would be visible at a distance of two to three feet if such light-emitting devices instead emitted visible light).

Conventional PPG sensors featuring square photodetector elements, such as the example shown in FIG. 1, may utilize two light sources that bracket the photodetector element so that the fall-off in illumination intensity that is evident in FIG. 4 may be mitigated—in such an arrangement, the light intensity along the left edge of the depicted area of FIG. 4 may be mirrored along the right edge of the depicted area, resulting in a valley of lower-intensity light near the middle of the square photodetector, but with both the left and right edges of the square photodetector seeing increased light intensity. This, however, requires that two LEDs be powered, instead of one, effectively doubling the power consumption attributable to the light sources.

The present inventors have determined that utilizing a HAR photodetector element, in some cases, can present a much more power-efficient technique for achieving increased sensor performance than the conventional approach of including multiple light sources, as a HAR photodetector element and single light source may achieve performance that is comparable or superior to the performance of a square photodetector with multiple light sources—thus avoiding the use of the extra light source (and avoiding the extra power consumption it would incur).

The present inventors have also determined that further increases in PPG sensor performance may be attained, in some cases, by arranging multiple HAR photodetectors in an array or pattern about a light source. Since the same light source may provide light to multiple HAR photodetectors, there is little or no additional power consumption attributable to the light source in such implementations as compared with implementations having only one photodetector element. The use of such HAR photodetector elements may also increase the signal to ambient noise ratio of the PPG sensor.

Figures 17, 18:
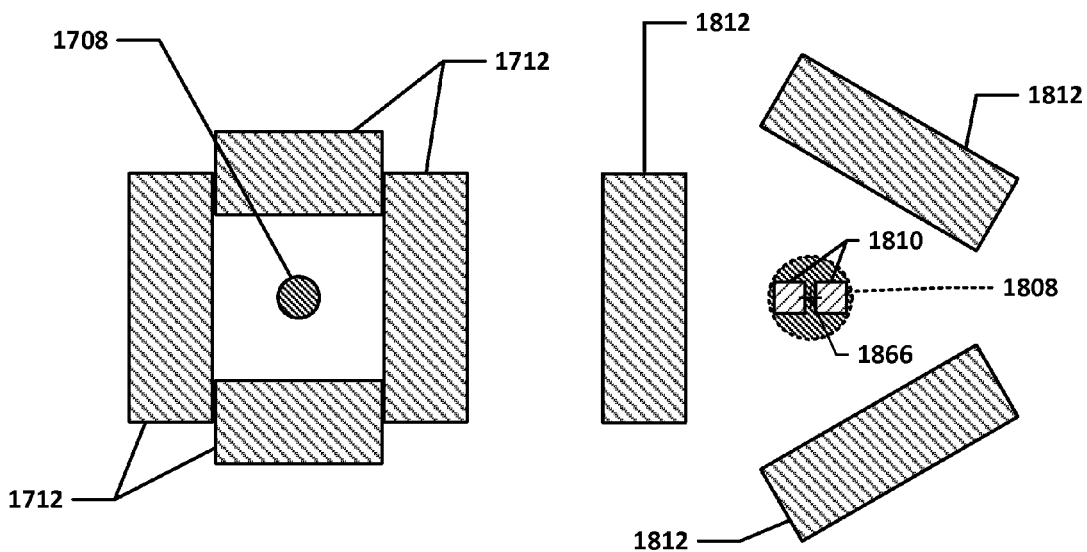

FIGS. 14 through 16 depict several examples of implementations with multiple HAR photodetectors, in accordance with several example implementations. In FIG. 14, two HAR photodetector elements 1412 are shown with a light source 1408 interposed midway between them. In FIG. 15, three HAR photodetector elements 1512 are shown in a circular array centered on a light source 1508. Similarly, in FIG. 16, four HAR photodetector elements 1612 are arranged in a circular array about a light source 1608. It is not necessary for the HAR photodetector elements in such patterns or arrays to be equidistantly-spaced, as is shown in the implementations of FIGS. 14, 15, and 16. For example, a three-element array may be formed by removing one of the photodetector elements 1612 from the array shown in FIG. 16. It is also not necessary for the photodetector elements within such a pattern or array to all be the same size and shape. For example, the upper and lower photodetector elements 1612 in FIG. 16 might have aspect ratios of 5:1, and the left and right HAR photodetector elements 1612 in FIG. 16 might have aspect ratios of 3:1 (which is the actual aspect ratio depicted). FIG. 17 depicts another example arrangement of photodetector elements. In FIG. 17, the upper and lower HAR photodetector elements 1612 may have aspect ratios of 2:1, and the left and right HAR photodetector elements 1612 may have aspect ratios of 3:1; in some such implementations, the shorter photodetector elements, e.g., the 2:1 aspect ratio photodetector elements 1712 in the depicted example, may be positioned with the midpoints of their shorter edges generally located along a line spanning between the short edges of the longer photodetector elements, e.g., the 3:1 aspect ratio photodetector elements 1712 in the depicted example. In some PPG implementations involving multiple HAR photodetector elements, the HAR photodetector elements may occupy more than 50% of an annular region about the light source that has an annular width of 1 mm.

FIG. 18 depicts an example of a PPG sensor photodetector layout as shown in FIG. 15 but with multiple light-emitting devices used in the light source, in accordance with an example implementation. As discussed earlier herein, a PPG sensor may utilize one or more light sources, each of which may include one or more light-emitting devices. As can be seen, the light source 1808 includes two light-emitting devices 1810, which may, for example, be surface-mount LEDs, one emitting primarily green-wavelength light and the other emitting primarily red-wavelength light. The two light-emitting devices 1810 may define a center point 1866 located midway between them, and may, in combination, be viewed as forming a light source 1808. It is to be understood that the light-emitting devices 1810 may be operated independently and may not be powered on simultaneously during actual use. As a result, the array of photodetector elements 1812 may not appear to be centered on the center of either light-emitting device 1810 when that light-emitting device 1810 is on, but the array of photodetector elements 1812 may, nonetheless, be considered to be centered on the light source 1808.

The present inventors have further determined that HAR photodetector elements, in at least some implementations, may be sized such that their width or the second maximum dimension of at least 90% of the active area of the HAR photodetector element is between approximately 0.5 mm and 1 mm; there may be some deviation from this range in some of these implementations, such as HAR photodetector elements where this dimension ranges between 0.45 mm and 1.1 mm.

Figure 19:
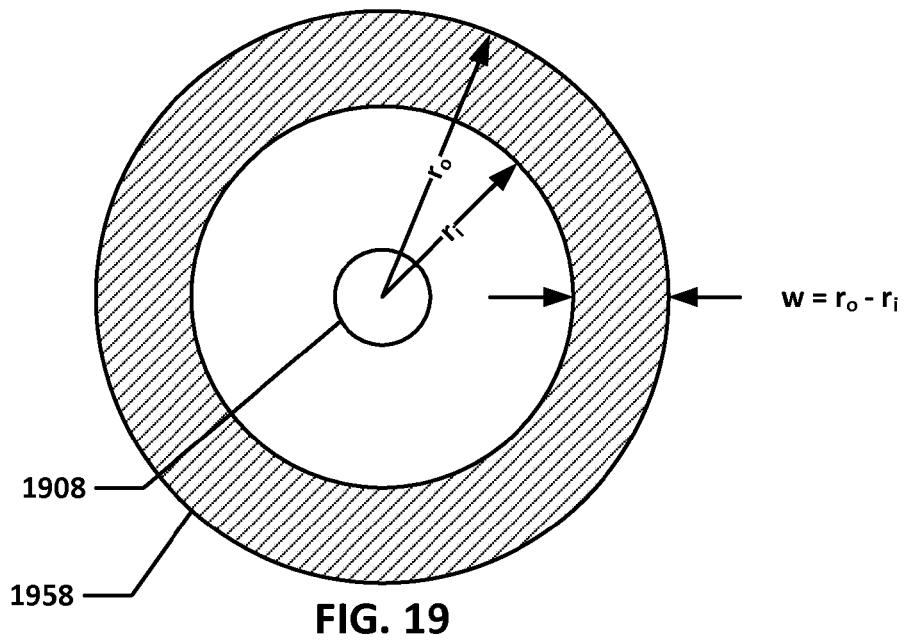
FIG. 19 shows an example light source and a surrounding annular region, in accordance with an example implementation.
Figure 20:
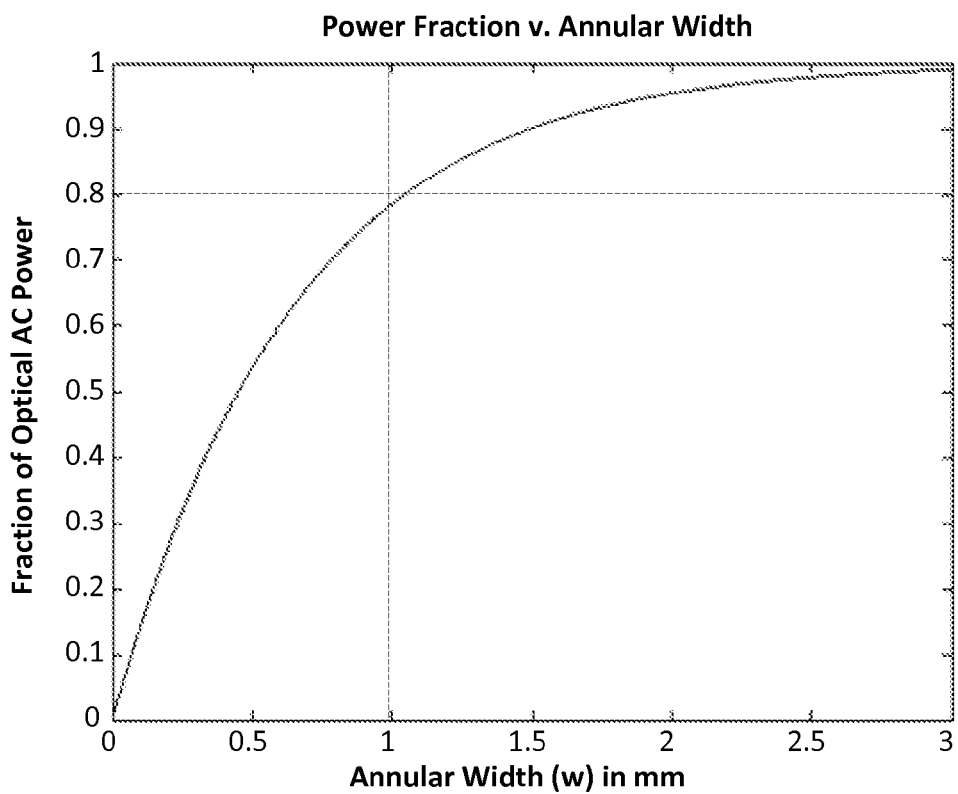
FIG. 20 depicts a plot of the fraction of the light intensity that is emanated outside of an arbitrary inner radius $r_i$ that would fall within the bounds of an annular region with an inner radius $r_i$ and an annular width as indicated along the x-axis, in accordance with an example implementation.

Generally speaking, the light intensity for light emanating from a person's skin from a PPG light source falls off in an axially symmetric manner with increasing distance from the center of the light source (this assumes a single light source PPG sensor). Accordingly, the light source may be surrounded by a plurality of concentric, annular regions that each correspond with a different average light intensity. The present inventors analyzed the characteristics of such annular regions and determined that, regardless of the inner radius of a particular annular region, approximately 80% of the available power or intensity of the emanated light available outside of the inner radius of the annular region occurs within 1 mm of the inner radius. Thus, any particular annular region with an annular width of approximately 1 mm will see approximately 80% of the light intensity/power that is available outside of the inner radius of that annular region. For clarity, the "annular width" (w) of an annular region is equal to the outer radius ($r_o$) of the annular region minus the inner radius ($r_i$) of the annular region. This is illustrated in FIG. 19, which shows a light source 1908 and a surrounding annular region 1958, in accordance with an example implementation; the inner radius $r_i$, the outer radius $r_o$, and the annular width of the annular region 1958 are indicated. FIG. 20 depicts a plot of the fraction of the light intensity that is emanated outside of an arbitrary inner radius $r_i$ that would fall within the bounds of an annular region with an inner radius $r_i$ and an annular width as indicated along the x-axis, in accordance with an example implementation. As can be seen, approximately 80% of the available light intensity falls outside the inner radius $r_i$ and within 1 mm of the inner radius $r_i$.

The present inventors determined that, given the high concentration of emanated light intensity within this 1 mm zone, sizing HAR photodetectors so as to have approximately a 1 mm width or less or such that the second dimension referenced above is approximately 1 mm or less may, in some implementations, offer enhanced performance in a PPG sensor.

Figure 21:
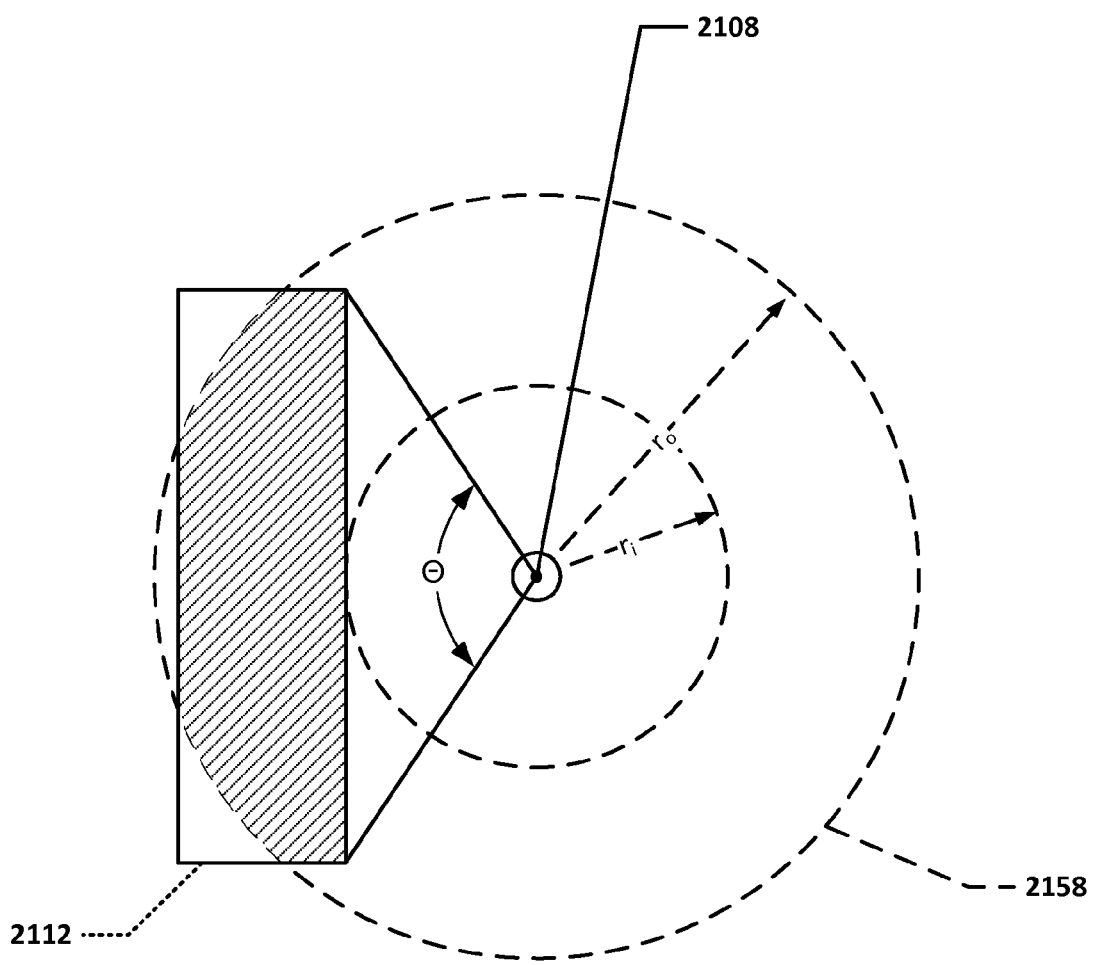
FIG. 21 depicts a light source, HAR photodetector, and various reference annotations.

In some implementations, HAR photodetector elements may be sized and arranged to satisfy certain geometric constraints. For example, in some implementations, the size of the HAR photodetector element may be constrained by certain geometric relationships, as described further below with respect to FIG. 21. FIG. 21 depicts a light source, HAR photodetector, and various reference annotations. In FIG. 21, a HAR photodetector element 2112 is shown positioned at a distance $r_i$ from a light source 2108. An annular region 2158 having an inner radius of $r_i$ and an outer radius of $r_o$ may be centered on the light source 2108. Generally speaking, the difference between $r_i$ and $r_o$ for the annular region 2158 in such implementations may be less than or equal to 2 mm. In addition to the relationship between $r_i$ and $r_o$ set forth above, the HAR photodetector element 2112 may subtend an angle θ at the light source center, as shown. In such circumstances, the HAR photodetector may be sized such that a) there is at least 80% overlap between the annular region 2158 and the HAR photodetector element 2112 (the overlap is indicated in FIG. 21 by diagonal cross-hatching; approximately 86% of the HAR photodetector 2112 in this example overlaps with the annular region 2158) and b) the angle θ is at least:

$$2 \cdot \arctan\left(\frac{1}{r_i}\right) \text{radians}$$

In some further implementations, the HAR photodetector 2112 may be further sized such that the angle θ is not more than:

$$2 \cdot \arctan\left(\frac{2.5}{r_i}\right) \text{radians}$$

Figure 22:
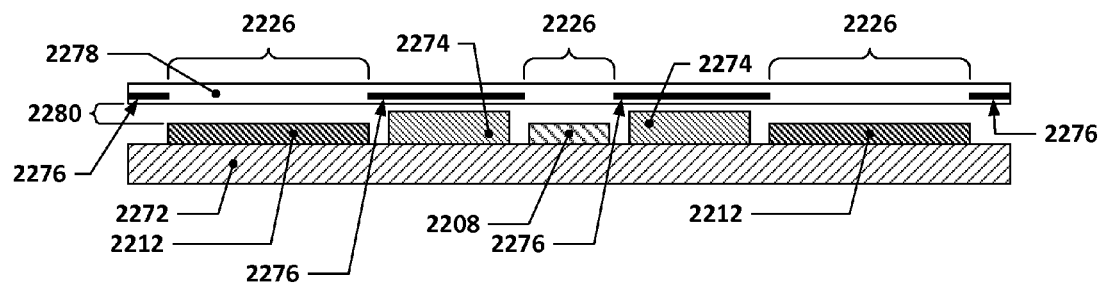
FIGS. 22 through 24 depict cross-sections of simplified representations of various PPG sensors, in accordance with various example implementations.
Figure 23:
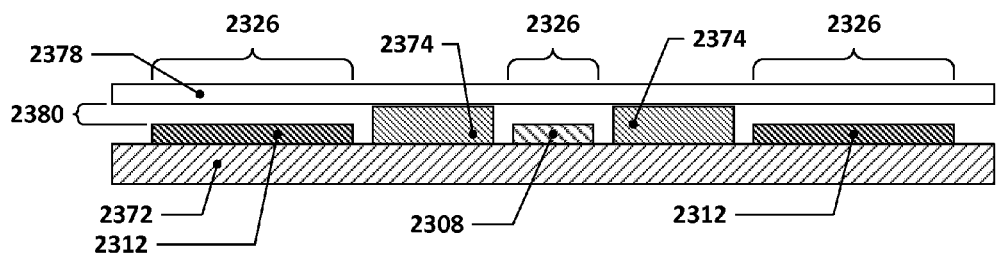
Figure 24:
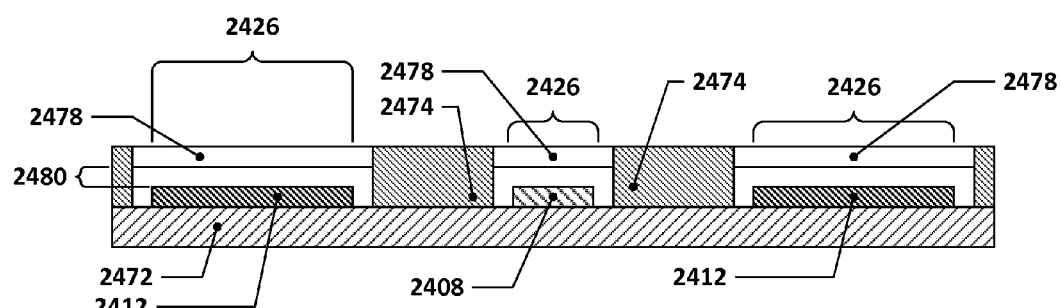

FIGS. 22 through 24 depict cross-sections of simplified representations of various PPG sensors, in accordance with various example implementations. Similar components in each of FIGS. 22 through 24 are indicated by numeric indicators having the last two digits in common, and may only be described once with respect to FIG. 22; this description is also applicable, however, to the corresponding elements in FIGS. 23 and 24.

In FIG. 22, a substrate 2272 supports two HAR photodetector elements 2212 that are positioned on either side of a light source 2208. A window 2278 is offset from the substrate 2272. The window 2278, in this implementation, is made from a translucent or transparent material, such as transparent acrylic, with an in-mold label 2276 embedded within it. The in-mold label 2276 may be black or otherwise rendered opaque to light to prevent light from entering or exiting the PPG sensor through the window 2278 except through window regions 2226. In other implementations, other masking techniques, such as a painted or silk-screened mask applied to the window 2278, may be used. Regardless of which technique is used, the in-mold label 2276 or the masking may prevent stray light from other sources, e.g., ambient light, from reaching the HAR photodetector elements 2212 and affecting the heart rate signal obtained by the PPG sensor. The window 2278 may be held against a person's skin, e.g., by being held in place with a strap, when heart rate measurements are obtained to allow light from the light source 2208 to shine through its associated window region 2226 and into the person's skin, where the light then diffuses into the surrounding flesh and is then emitted back out of the person's skin and into the HAR photodetector elements 2212 through the respective window regions 2226 associated with the HAR photodetector elements 2212.

In order to reduce the chance that light from the light source 2208 will reach either of the HAR photodetector elements 2212 without first being diffused through the person's skin, the light source 2208 may be separated from the HAR photodetector elements 2212 within the PPG sensor by walls 2274, which may extend to the window 2278 or may stop short of the window 2278. In some implementations, an adhesive gap filler, e.g., black silicone, may be used to bridge any gap remaining between the walls 2274 and the window 2278. A gap 2280 may exist between the window 2278 and the HAR photodetector elements 2212 in some implementations, although in other implementations, this gap may be eliminated and the HAR photodetector element 2212 may be butted up against the window 2278. The walls 2274 may prevent light from the light source 2208 from reaching the HAR photodetector elements 2212 by following paths completely within the housing of the PPG sensor. As can be seen, the window regions 2226 through which the light reaches the HAR photodetector elements 2212 each overlap their respective HAR photodetector elements 2212. In the depicted example, the window regions 2226 are mutually coextensive with their respective HAR photodetector elements 2212, although in other implementations, the window regions 2226 may be smaller or larger than their respective HAR photodetector elements 2212, e.g., to accommodate assembly tolerance mismatch.

FIG. 23 depicts a PPG sensor implementation that is similar to the PPG sensor of FIG. 22 except that the window 2378 does not include any masking, for example, in the form of an in-mold label, such as in-mold label 2276. In FIG. 23, the walls 2374 also extend closer to the window 2378. In FIG. 23, the window 2378 is optically transparent across the entire depicted span.

FIG. 24 depicts a PPG sensor implementation that is similar to the PPG sensor implementation of FIGS. 22 and 23, except that the contiguous windows 2278 and 2328 have been replaced with discrete windows 2478. In this implementation, each window 2478 may have its own window region 2426 that overlaps with a different one of the light source 2408 or the HAR photodetector elements 2412. In such implementations, the windows 2478 may be glued or otherwise held in place within a frame that may supply the walls 2474. Alternatively, the windows 2478 may be formed by filling the recesses formed by the walls 2474 and other surrounding structure with a clear, flowable material, such as epoxy, and then allowing the flowable material to cure and harden. In such implementations, the gap 2480 may not exist since the flowable material may encapsulate the HAR photodetector elements 2412.

Regardless of the particular manner in which the window regions 2226, 2326, or 2426 are provided, the window regions overlap with the HAR photodetector elements such that light that enters the PPG sensor via the window regions generally takes a direct route to the HAR photodetector element, as compared with a route that involves forcing the light to travel in a direction parallel to the window, as may be done with various types of optical light guides. The phrase "optical light guide," as used herein with respect to PPG sensors, refers to particular types of optical structures that redirect or transport the light that enters through a surface within a first region of the surface such that a majority of that light is transported in a direction generally transverse to the surface to an area overlapped by a second region of the surface that is offset from the first region along the surface. Optical light guides, as the term is used herein, are not to be confused with other optical structures, such as microlens arrays or lenses that may be placed over a HAR photodetector element to improve collection efficiency, optical windows that may slightly refract light that passes through the windows but that do not transport or redirect light in a significant manner in directions transverse to the surface, optical filters that may simply filter light of certain wavelengths, etc. In some implementations of the PPG sensors discussed herein, there is no need for optical light guides since the HAR photodetector elements are generally overlapped by the window regions.

The above concepts have been discussed primarily with respect to light sources that emit green light, e.g., wavelengths in the range of 500 nm to 550 nm, although it is contemplated that the photodetector element concepts discussed herein may see similar performance with light sources that emit light predominantly in the 500 nm to 600 nm range, which includes yellow light as well as some light orange light. Light sources emitting light in the green spectrum are particularly well-suited for photoplethysmographic techniques for measuring heart rate. In contrast, other photoplethysmographic techniques, such as techniques for measuring blood oxygenation levels, may be most effective using light of dramatically different wavelengths, such as in the red wavelengths, e.g., 660 nm, or in the infrared spectrum. The aspect ratios and dimensional values discussed herein are tailored based on the green/yellow light spectrum and are not tailored for use in other spectrums, such as the red or infrared spectra.

While the concepts discussed herein are thought to be applicable to a variety of different sizes of photodetectors, the concepts are particularly applicable to PPG implementations for wearable fitness monitoring devices. Generally speaking, such devices, which are often designed to be worn as bracelets or wristbands, have a small housing that has a limited area that is in contact with a persons' skin. As a result, there are practical upper limits in such implementations on how the light source(s) and photodetector element(s) of a PPG sensor may be arranged and sized. Typically speaking, the light source(s) and photodetector element(s) of such implementations may be arranged such that the photodetector element(s) are positioned with the edge closest to the light source located between 1 mm to 4 mm from the center or edge of the light source. However, it is to be understood that implementations discussed herein may be used in products that achieve closer or farther spacing from the light source center, such as spacing closer than 1 mm or farther than 4 mm.

In some implementations, the HAR photodetector elements that may be used in a PPG may be positioned with the edge closest to the light source of the PPG sensor offset from the center of the light source by between 1 mm and 4 mm and may be sized such that they have a maximum first dimension substantially between 1 mm and 5 mm and a maximum second dimension substantially between 0.05 mm and 2 mm, while being consistent with the aspect ratio of the maximum first dimension to the maximum second dimension being substantially between 2:1 to 5:1.

While the photodetector element may be positioned with its closest edge further than 4 mm from the center of the light source, doing so may prove counterproductive, as a higher-intensity light source may be needed to ensure that sufficient light is diffused across the increased distance in order to obtain a sufficiently strong signal at the photodetector. As a higher-intensity light source will generally consume additional power, such a compromise may be undesirable in a wearable fitness monitor context.

Figure 25:
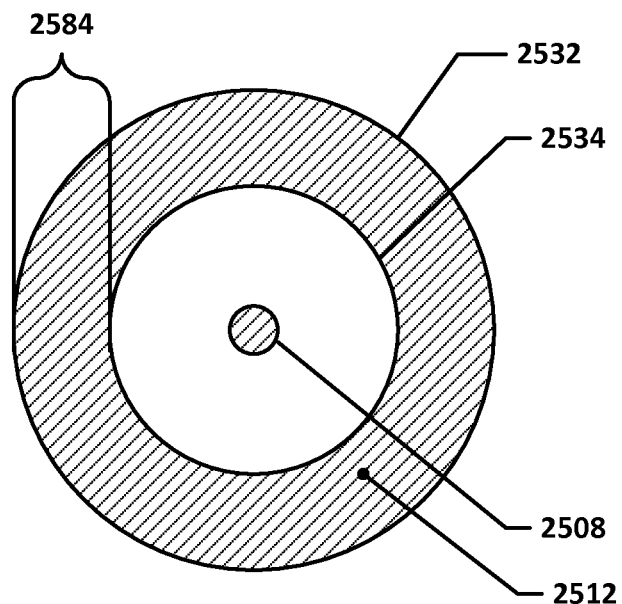
FIG. 25 depicts an example of an annular photodetector element with a light source in the middle, in accordance with an example implementation.
Figure 26:
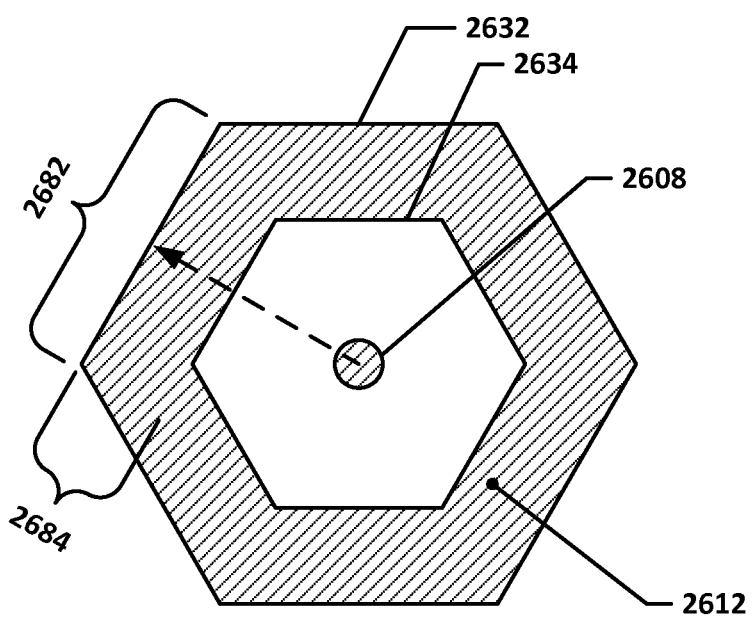
FIG. 26 depicts an example of a polygonal photodetector element with a light source in the middle, in accordance with an example implementation.

In addition to the HAR photodetectors discussed herein, performance increases over square-photodetector-based PPGs for heart rate measurement may be realized through the use of non-HAR and non-square photodetector elements that generally encircle the light source and that have a central opening in the middle for the light source to shine through. Generally speaking, such photodetector elements may have an exterior periphery that is defined by a first boundary, and a second boundary, within the first boundary, that defines the central opening. FIGS. 25 and 26 depict two example implementations of such PPG sensors.

FIG. 25 depicts an example of an annular photodetector element 2512 with a light source 2508 in the middle, in accordance with an example implementation. The annular photodetector element 2512 may have an exterior periphery defined by a first boundary 2532 and a central opening defined by a second boundary 2534; the first boundary 2532 and the second boundary 2534 may be offset from one another by a first distance 2584 along a radius of the annular area. The light source 2508 may be a green wavelength light source that predominantly emits light between 500 nm and 550 nm or between 500 nm and 600 nm in wavelength. Such a photodetector element 2512 may be sized such that the ratio of the circumference of the second boundary 2534 to the first distance 2584 is between 9.5:1 and 11.5:1. In some implementations, the annular photodetector element 2512 may be sized such that the first boundary has a diameter of between 3 mm to 5.5 mm and the second boundary has a diameter of between 1 mm to 2.5 mm. These parameters are believed to provide good light-gathering performance for heart rate measurement purposes when used with green-wavelength light.

FIG. 26 depicts an example of a polygonal photodetector element 2612 with a light source 2608 in the middle, in accordance with an example implementation. As with the annular photodetector element 2512, the polygonal photodetector element 2612 may have an exterior periphery defined by a first boundary 2632 and a central opening defined by a second boundary 2634. In this case, however, the first boundary 2632 and the second boundary 2634 are both polygonal in nature, e.g., a six-sided polygon. Other polygonal shapes may be used for other implementations, such as triangular shapes, square shapes, pentagonal shapes, septagonal shapes, octagonal shapes, and so on, i.e., N-sided polygons. The edges of the first boundary 2632 and the second boundary 2634 may be offset from one another by a first distance 2684 along an axis perpendicular to the edges. In such implementations, each side of the polygon forming the second boundary 2634 may have a second length 2682, and the ratio of the second length 2682 to the first distance 2684 may be between 2:1 to 5:1. These parameters are believed to provide good light-gathering performance for heart rate measurement purposes when used with green-wavelength light.

It is to be understood that reference herein to "control logic" refers to hardware and/or software that may be used to provide certain functionality, such as controlling when the light source(s) of a PPG is on or off, controlling the intensity with which the light source(s) is illuminated, collecting data from one or more photodetectors, and analyzing at least the data collected from the one or more photodetectors in order to determine a measurement of a person's heart rate. Control logic may include, for example, one or more processors and a memory that stores computer-executable instructions for controlling the one or more processors to provide such functionality. The control logic may also include various circuit elements that may provide aspects of such functionality without need for computer-executable instructions stored in memory. In some implementations, the control logic may be provided, at least in part, by an application-specific integrated circuit (ASIC).

Figure 27:
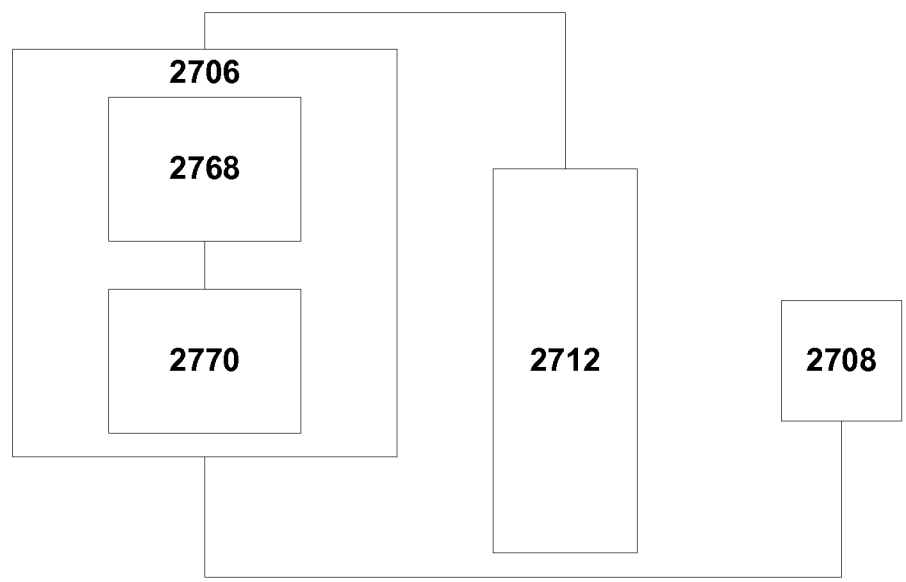
FIG. 27 depicts a high-level block diagram of a PPG sensor, in accordance with an example implementation.

FIG. 27 depicts a high-level block diagram of a PPG sensor, in accordance with an example implementation. In FIG. 27, control logic 2706 is shown, which includes a processor 2768 and a memory 2770, which are operatively coupled with one another. The control logic is operatively coupled with a light source 2708 and a photodetector element 2712. The control logic 2706 may thus cause the light source 2708 to emit light at desired times, and may receive a signal indicative of an amount of detected light from the photodetector element 2712.

There are many inventions described and illustrated herein. While certain implementations, features, attributes and advantages of the inventions have been described and illustrated, it should be understood that many others, as well as different and/or similar implementations, features, attributes and advantages of the present inventions, are apparent from the description and illustrations. As such, the above implementations of the inventions are merely exemplary. They are not intended to be exhaustive or to limit the inventions to the precise forms, techniques, materials and/or configurations disclosed. Many modifications and variations are possible in light of this disclosure. It is to be understood that other implementations may be utilized and operational changes may be made without departing from the scope of the present inventions. As such, the scope of the inventions is not limited solely to the description above because the description of the above implementations has been presented for the purposes of illustration and description.

In particular, it is to be understood that any of the implementations discussed above with respect to a single photodetector element spaced apart from a light source may also be implemented using a plurality of photodetector elements arranged about the light source, as discussed with respect to various other implementations discussed herein.

Furthermore, it is to be understood that the use of the term "substantially" herein, unless otherwise defined with respect to a specific context, with respect to a numeric quantity or otherwise quantifiable relationship, e.g., perpendicularity or parallelism, is to be understood as indicating that quantity ±10%. Thus, for example, lines that are substantially perpendicular to one another may be at angles between 81° and 99° to one another. In a further example, dimensions that are substantially between 1 mm and 3 mm, for example, may range from 0.9 mm to 3.3 mm. In another example, an angle that is substantially in the range of 1 to 1.1 radians may be between 0.9 radians and 1.21 radians.

Importantly, the present invention is neither limited to any single aspect nor implementation, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

What is claimed is:

1. An apparatus comprising:
   a light source;
   one or more discrete photodetector elements, each photodetector element having:
      a first edge having a first length, and
      a first width in a direction perpendicular to the first edge; and
   control logic, the control logic communicatively connected with the light source and each photodetector element and configured to:
      cause the light source to emit light,
      obtain one or more measured light intensity measurements from the one or more photodetector elements, and
      determine a heart rate measurement based, at least in part, on the one or more light intensity measurements,
      wherein the ratio of the first length to the first width of each photodetector is substantially between 2:1 to 5:1.

2. The apparatus of claim 1, wherein:
   the first edge of each photodetector element is perpendicular to an axis radiating out from a center of the light source.

3. The apparatus of claim 1, wherein:
   the first edge of each photodetector element is transverse to an axis radiating out from a center of the light source.

4. The apparatus of claim 1, wherein:
   the light source includes a plurality of light-emitting devices.

5. The apparatus of claim 4, wherein:
   the plurality of light-emitting devices includes at least two light-emitting devices that predominantly emit light of different wavelengths.

6. The apparatus of claim 4, wherein:
   there are a plurality of photodetector elements arranged in a pattern, and
   the plurality of light-emitting devices is collocated at a center point of the pattern of photodetector elements.

7. The apparatus of claim 6, wherein the ratio of the first length to the first width of each photodetector element is substantially between 2:1 to 3.5:1.

8. The apparatus of claim 1, wherein the ratio of the first length to the first width of each photodetector element is substantially between 3.5:1 to 5:1.

9. The apparatus of claim 1, wherein each photodetector element:
   has a first length between 1 mm and 5 mm and a first width between 0.5 mm and 2 mm, with the ratio of the first length to the first width substantially between 2:1 to 5:1, and
   is positioned such that an edge of the photodetector element closest to the light source is between 1 mm and 4 mm from the light source.

10. The apparatus of claim 9, wherein the pattern of photodetector elements includes three photodetector elements that are equidistantly spaced about the light source.

11. The apparatus of claim 1, further comprising:
    a housing having a back face that includes one or more transparent window regions through which light may enter the apparatus, wherein:
       each photodetector element is positioned such that that photodetector element is overlapped by a corresponding one of the one or more transparent window regions, and
       the housing is configured such that the back face is adjacent to the skin of a person wearing the apparatus when the apparatus is worn by that person.

12. The apparatus of claim 11, wherein:
    the back face includes a thin window, and
    the window regions are sub-regions of the window that are defined by the photodetector elements.

13. The apparatus of claim 11, wherein:
    each photodetector element is offset from the corresponding transparent window region by a corresponding gap in a direction normal to the photodetector element, and
    the gap is free of optical light guides.

14. The apparatus of claim 1, wherein each photodetector element has, in addition to the first edge, an arcuate second edge opposite the first edge, wherein the arcuate second edge has a maximum distance from the first edge, when measured along a direction perpendicular to the first edge, that is equal to the first width.

15. An apparatus comprising:
    a first light source;
    a second light source;
    a photodetector element interposed between the first light source and the second light source; and
    control logic, the control logic communicatively connected with the first light source, the second light source, and the photodetector element and configured to:
       cause the first light source and the second light source to emit light,
       obtain measured light intensity measurements from the photodetector element, and
       determine a heart rate measurement based, at least in part, on the light intensity measurements,
    wherein:
       the photodetector element is rectangular in shape, has a first edge with a first length, and has a second edge, perpendicular to the first edge, with a second length, and
       the ratio of the first length to the second length is substantially between 2:1 to 5:1.

16. The apparatus of claim 15, wherein:
    the first edge of each photodetector element is perpendicular to an axis spanning between a center of the first light source and a center of the second light source.

17. The apparatus of claim 15, wherein:
    the first edge of each photodetector element is transverse to an axis spanning between a center of the first light source and a center of the second light source.

18. The apparatus of claim 15, further comprising
    a housing having a back face that includes a transparent window region that overlaps the photodetector element and two further window regions that are each associated with a different one of the first light source and the second light source and that allow light from the associated light source to pass through the back face, wherein:

the first light source and the second light source are the only light sources in the apparatus configured to emit light through the back face, and the housing is configured such that the back face is adjacent to the skin of a person wearing the apparatus when the apparatus is worn by that person.

19. The apparatus of claim 15, wherein the photodetector element is equidistant from the first light source and the second light source.

20. An apparatus comprising:

a light source;

one or more photodetectors, each photodetector having a photosensitive area, wherein at least 90% of the photosensitive area is defined by a first dimension along a first axis and a second dimension along a second axis perpendicular to the first axis; and control logic, the control logic communicatively connected with the light source and each photodetector and configured to:

cause the light source to emit light, obtain one or more measured light intensity measurements from the one or more photodetectors, and determine a heart rate measurement based, at least in part, on the one or more light intensity measurements, wherein, for each photodetector:

the ratio of the first dimension to the second dimension is substantially between 2:1 to 5:1.

21. The apparatus of claim 20, wherein:

the light source includes a plurality of light-emitting devices, and the plurality of light-emitting devices includes at least two light-emitting devices that predominantly emit light of different wavelengths.

22. The apparatus of claim 20, wherein:

the one or more photodetectors includes a plurality of photodetectors arranged in a pattern, and the light source is located at a center point of the pattern of photodetectors.

23. The apparatus of claim 20, wherein the ratio of the first dimension to the second dimension of each photodetector is substantially between 2:1 to 3.5:1.

24. The apparatus of claim 20, wherein the ratio of the first dimension to the second dimension of each photodetector is substantially between 3.5:1 to 5:1.

25. The apparatus of claim 20, wherein:

the one or more photodetectors includes a plurality of photodetectors arranged in a pattern, and the center of the photosensitive area of each photodetector in the pattern is equidistant from the center of the light source.

26. The apparatus of claim 25, wherein:

the first dimension associated with each photodetector is between 3 mm and 5 mm and the second dimension associated with each photodetector is between 1 mm and 2 mm, consistent with the ratio of the first dimension to the second dimension being between 2:1 to 5:1, and each photodetector is positioned such that an edge of the photosensitive area for that photodetector that is closest to the light source is between 1 mm and 4 mm from the center of the light source.

27. The apparatus of claim 26, wherein the pattern of photodetectors includes four photodetectors that are equidistantly spaced about the light source.

28. The apparatus of claim 20, further comprising:

a housing having a back face that includes one or more thin, transparent window regions, wherein:

each photodetector is positioned such that the photosensitive area of that photodetector is overlapped by a corresponding one of the transparent window regions, and the housing is configured such that the back face is adjacent to the skin of a person wearing the apparatus when the apparatus is worn by that person.

29. The apparatus of claim 28, wherein:

the back face includes a thin window, and the window regions are sub-regions of the window that are defined by the photosensitive areas of the one or more photodetectors.

30. The apparatus of claim 28, wherein:

the photosensitive area of each photodetector is offset from the corresponding transparent window region by a corresponding gap in a direction normal to the photodetector, and the gap is free of optical light guides.

* * * * *